(12) United States Patent
Lee

(10) Patent No.: US 8,848,872 B2
(45) Date of Patent: Sep. 30, 2014

(54) DIGITAL RADIOGRAPHY SYSTEM

(76) Inventor: Jong In Lee, Wonju-si (KR)

( * ) Notice: Subject to any disclaimer, the term of this patent is extended or adjusted under 35 U.S.C. 154(b) by 915 days.

(21) Appl. No.: 12/995,080

(22) PCT Filed: May 29, 2009

(86) PCT No.: PCT/KR2009/002869
§ 371 (c)(1),
(2), (4) Date: Nov. 29, 2010

(87) PCT Pub. No.: WO2009/145584
PCT Pub. Date: Dec. 3, 2009

(65) Prior Publication Data
US 2011/0110494 A1    May 12, 2011

(30) Foreign Application Priority Data

May 30, 2008  (KR) .................. 10-2008-0050616
Apr. 15, 2009  (KR) .................. 10-2009-0032765

(51) Int. Cl.
*H05G 1/64* (2006.01)
*A61B 6/00* (2006.01)
*G03B 42/04* (2006.01)

(52) U.S. Cl.
CPC ..................................... *G03B 42/04* (2013.01)
USPC ........ 378/91; 378/98.8; 378/116; 250/370.09

(58) Field of Classification Search
USPC ..................... 378/91, 98.8, 115, 116, 189; 250/370.09
See application file for complete search history.

(56) References Cited

U.S. PATENT DOCUMENTS

| | | | | |
|---|---|---|---|---|
| 5,844,961 A | * | 12/1998 | McEvoy et al. | 378/98.8 |
| 5,877,501 A | * | 3/1999 | Ivan et al. | 250/370.09 |
| 6,370,229 B1 | * | 4/2002 | Tsuchino et al. | 378/165 |
| 6,501,827 B1 | * | 12/2002 | Takasawa | 378/116 |
| 6,707,880 B2 | * | 3/2004 | Yamayoshi | 378/92 |
| 6,859,521 B2 | * | 2/2005 | Spahn | 378/117 |
| 7,197,112 B2 | * | 3/2007 | Maschke | 378/91 |
| 7,298,825 B2 | * | 11/2007 | Omernick et al. | 378/116 |
| 7,545,914 B2 | * | 6/2009 | Kito et al. | 378/98.8 |
| 7,785,005 B2 | * | 8/2010 | Bettouyashiki et al. | 378/189 |
| 7,909,511 B2 | * | 3/2011 | Hall | 378/189 |

FOREIGN PATENT DOCUMENTS

| | | |
|---|---|---|
| JP | 2002-336225 A | 11/2002 |
| JP | 2008-220724 A | 9/2008 |
| KR | 10-2004-0054791 A | 6/2004 |

OTHER PUBLICATIONS

International Search Report, Application No. PCT/KR2009/002869, dated Jan. 2, 2010.

* cited by examiner

*Primary Examiner* — Allen C. Ho
(74) *Attorney, Agent, or Firm* — Kile Park Reed & Houtteman PLLC

(57) ABSTRACT

Disclosed herein is a digital radiography system which provides detachable and portable flat panel detectors (hereinafter, referred to as 'electronic cassettes') and transreceives data recorded in the electronic cassettes in on-line through a network. The digital radiography system includes bucky trays on which a plurality of portable electronic cassettes is detachably mounted, and a workstation connected with the bucky trays through communication to identify the plurality of portable electronic cassettes mounted on the bucky trays and to download pre-processing files of the identified electronic cassettes through the network or a portable storage device or to store files, generated by the plurality of electronic cassettes, in the storage device.

16 Claims, 19 Drawing Sheets

(a)  (b)

FIG. 11
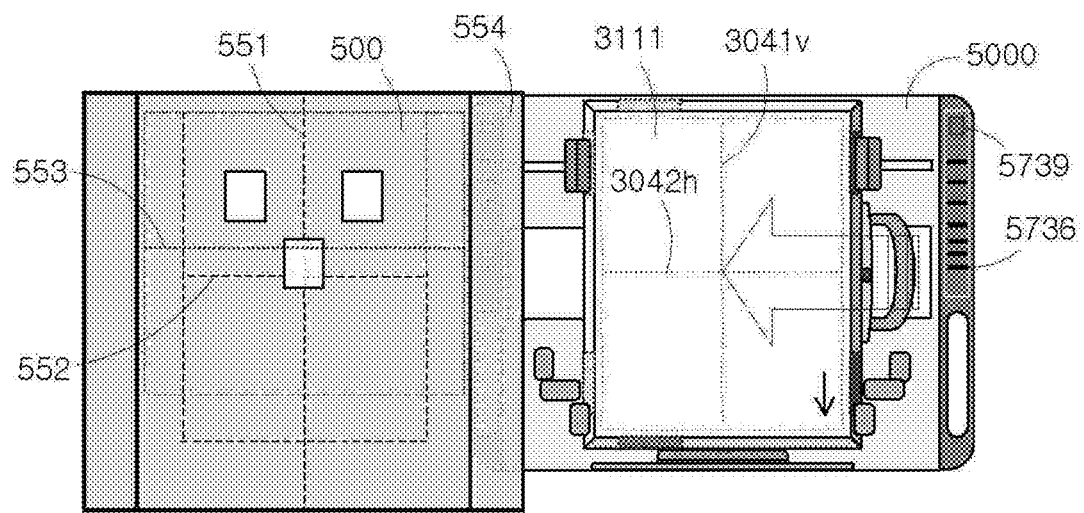
(a)
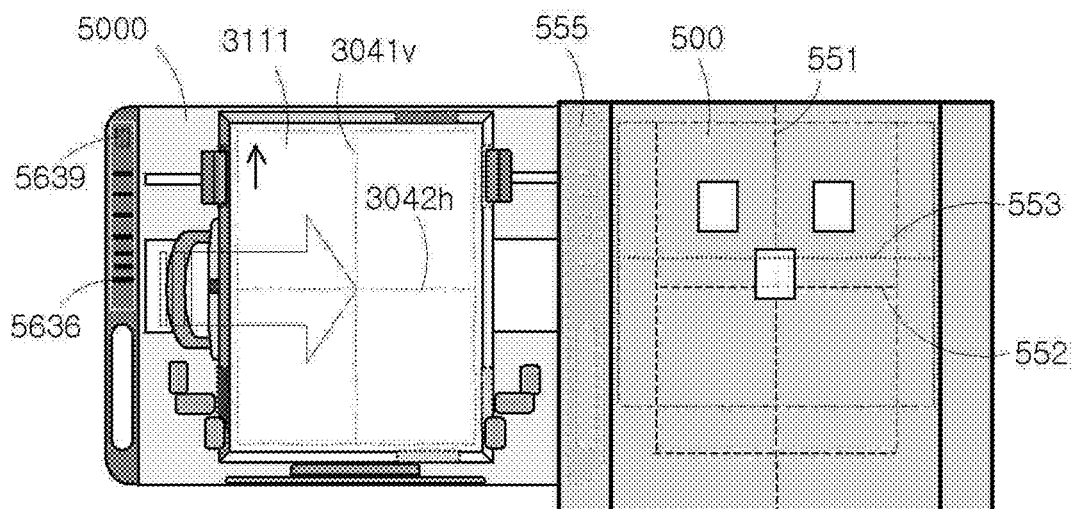
(b)

FIG.13
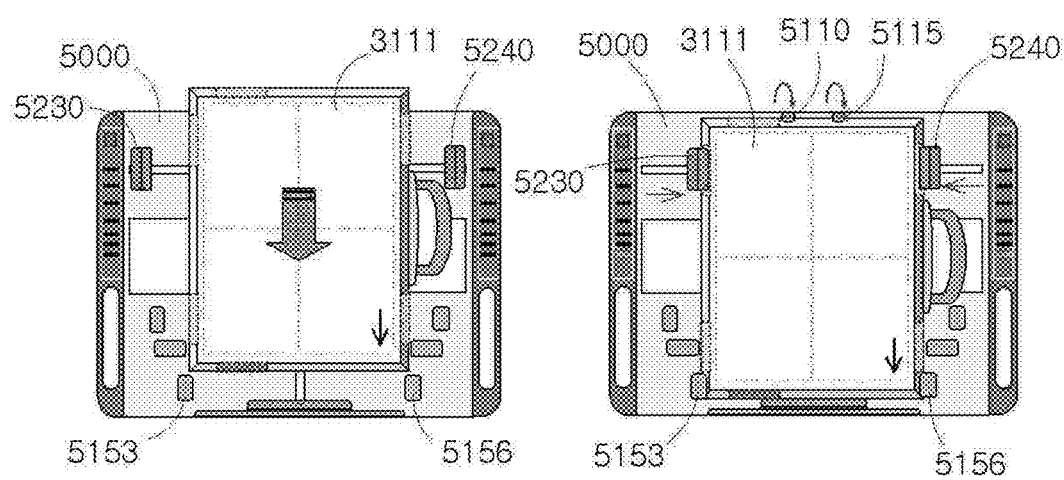
(a)　　　　　　　　　(b)
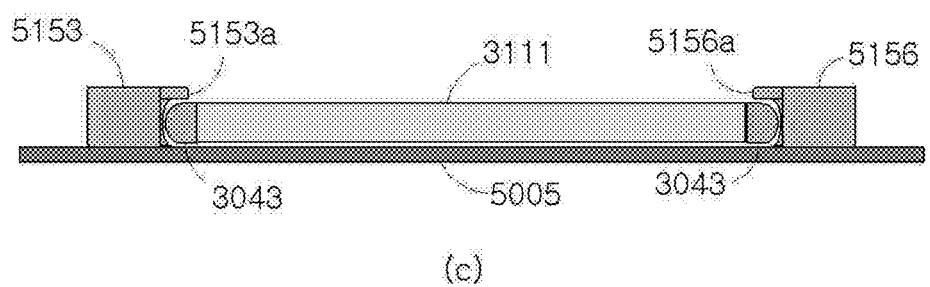
(c)

(a)　　　　　　　　(b)

DIGITAL RADIOGRAPHY SYSTEM

TECHNICAL FIELD

The present invention relates to a digital radiography system used in a medical imaging system, and more particularly to a digital radiography system which provides detachable and portable flat panel detectors (hereinafter, referred to as 'electronic cassettes') and transreceives data recorded in the electronic cassettes in on-line through a network or off-line.

BACKGROUND ART

In general, radiography systems for medical diagnosis irradiate X-rays onto a human body and detect an energy intensity distribution difference between the X-rays transmitted by the human body. Detection methods of these radiography systems are divided into an analog type and a digital type.

In the analog detection method, an intensifying screen (a fluorescent plate) which emits light when it receives X-rays and a silver salt film are combined, a latent image is formed on the silver salt film using the light generated by the intensifying screen, and then chemical treatment is carried out on the silver salt film, thereby obtaining a visible image. In order to perform such a method, the intensifying screen and the silver salt film are kept in a dark condition, and a film cassette is used in radiography.

In the above analog detection method, consumable costs of the film are continuously generated during a development process, the film is used to perform all processes, such as image acquisition, display, storage, and transmission media, and thus requires close attention and causes a difficulty in maintenance of the film, increase of maintenance costs, and a lot of risk of loss and damage, a development waste liquid causes environmental pollution and thus obstructs hospital environments, and time consumption due to the development process delays a consultation time of a patient and thus improvement in medical service environments is urgently required.

In the digital detection method, a two-dimensional sensor is provided as a detection medium responding to X-rays, a minute electrical signal generated by the sensor is obtained through a two-dimensional matrix and is amplified by an amplification circuit, the signal amplified by the amplification circuit is converted into a digital value by an analog/digital converter, the digital value is changed into an image data, and the image data undergoes proper image pre-processing for optimal visualization and is then displayed on a monitor or a printer.

Representative detectors employing the above method include Computer Radiography (CR) using image plates, a CCD detector using a scintillator and a Charge-Coupled Device (CCD), a flat panel detector using a thin film transistor, and so on. Among these detectors, a digital X-ray image obtaining method using the flat panel detector has been increasingly used now in consideration of image quality, reduction in an amount of radiation exposed to a patient, efficiency in inspection, and easiness in mount.

An ideal flat panel detector must have high contrast resolution and high spatial resolution at a proper amount of radiation so as to provide an image of a high quality. Further, the ideal flat panel detector must have high time resolution, achieve imaging at a large area of more than 14×17 inches, and have a matrix having 2000 pixels in the horizontal axis direction and 2000 pixels in the vertical axis direction with a pixel size of less than 200 μm. Moreover, the detector must have a strong frame, use semiconductor, and have a size equal to that of an intensifying screen/film cassette and proper weight and performance.

Conventional flat panel detectors used for the clinical purpose mostly satisfy the above requirements, but are not satisfactory in size and weight and are used only in a state in which the flat panel detectors are fixed to the inside of a table bucky or a stand bucky, thus causing several problems, as follows.

First, special radiography techniques for diagnosis are limited. For example, the fixed flat panel detectors are fixed to the inside of the closed table bucky and the closed stand bucky, X-rays generated from an X-ray tube head are irradiated downwards and are transmitted by a patient, and the fixed flat panel detector fixed to the inside of the closed table bucky detects the transmitted X-rays. However, since movement of the fixed flat panel detector is restricted, radiography in the horizontal direction or radiography in the axial direction is not performed or radiography is performed only in an inconvenient pose of a patient, and thus acquisition of a diagnostically valuable image is limited. Particularly, if a serious patient or an emergent patient needs to be radiographed as being located on a portable patient bed, the digital radiography system using the fixed flat panel detectors cannot perform radiography of such a patient.

In order to solve such a problem, the conventional digital radiography system using the fixed flat panel detectors must be used together with Computer Radiography (CR) equipment using image plates.

The image plate is used under the condition that it is mounted on a protective case referred to as a cassette and having the same shape and weight as those of a film cassette using the intensifying screen and the film, thereby providing familiarity to users having used the film cassette. Further, the image plate has a weight of about 1~3 kg, and thus may be applied to various radiography postures using a simple fixing device. The image plate has a latent image generated by radiography, and the latent image is read by an image reader and is converted into a final image through analog/digital conversion and image processing. However, the image plate is deteriorated according to the number of times of radiography, and needs to be replaced with a new one through image deterioration measurement.

If both radiography using the flat panel detector and radiography using the image plate are performed with respect to one patient, diagnosis through comparison between two digital images is very difficult. Since the two detectors are different in aspects of characteristics and image processing techniques thereof, it is difficult for an image reading doctor to diagnose the patient through comparison between the two digital images.

Second, a grid to remove scattered radiation generated from a subject for radiography due to X-ray irradiation is fixed to the bucky. The grid is used even in radiography which generates a small amount of scattered radiation and thus does not require the grid.

The grid serving to remove the scattered radiation reaching an X-ray detection medium includes a lead foil plate and aluminum (or paper or carbon). The grid removes primary rays required to form a precise image as well as removes the scattered radiation. If the grid is fixed to the bucky, the grid must be used even in radiography not requiring the grid, and thus radiography conditions are raised as much as a sufficient amount of primary rays due to use of the grid, thereby causing increase in an amount of radiation exposed to a patient and raise in load of an X-ray tube. In order to improve these problems, some equipments are provided with buckies designed such that grids may be detachably attached to the buckies.

Third, the fixed flat panel detector is fixed to the inside of the bucky, and thus all radiography images are enlarged (iPs/Ps, Ps: size of subject for radiography, iPs: image size).

As a radiography image for medical diagnosis, an image having the precisely same size as that of a human body (Ps=iPs) without enlargement is required. In order to minimize image enlargement, a distance Dfo between an X-ray focus and a patient is maximally elongated and a distance Dod between the patient and the detector is minimized. In radiography on a table, since a distance D fod between the X-ray focus and the detector is defined as 100 cm, in order to minimize image enlargement, the distance Dod between the patient and the detector is minimized, but the fixed flat panel detector is mounted within the bucky and thus minimization of the distance Dod is limited.

Fourth, if the detector is replaced, it takes a long time to complete the replacement until service complement.

If the fixed flat panel detector is out of order during using the equipment and cannot be used, the digital radiography system cannot be used, and a time for service engineer call, a time for detachment of the flat panel detector and mount of a new flat panel detector and for detector stabilization, and a time for image correction file generation of the detector (for calibration) are required. Therefore, the expensive digital radiography system cannot be used for a long period of time.

Recently, in order to solve the problems of the digital radiography system using the fixed flat panel detectors, a digital radiography system using portable flat panel detectors (hereinafter, referred to as 'electronic cassettes') is being used. The electronic cassettes must be small-sized and lightweight in consideration of mobility and operability, and particularly, in order to apply the electronic cassettes to the conventional radiography systems using image plate cassettes or film cassettes, a specific structure of the electronic cassettes needs to be designed.

Particularly, the electronic cassette selects a wireless data transmission method in order to assure autonomy thereof, requires a storage battery for power supply, and requires a special structure to minimize damage due to external impact according to autonomy and a special design to be interchanged with the conventional image plate cassette or film cassette in the bucky of the radiography system. Thereby, the size and weight of the electronic cassette are increased, and particularly, if the number of times of radiography is increased, the storage battery needs to be designed so as to have a high capacity and thus special configuration and structure are required so as to satisfy miniaturization and lightweight requirements of the electronic cassette.

Further, in case of the conventional image plate cassette or film cassette, when radiography is performed under the condition that the conventional image plate cassette or film cassette is mounted within the bucky, a latent image, which is recorded on the image plate of the image plate cassette and the film of the film cassette, is converted into a final image by the image plate reader or a film developing unit after the cassette is detached from the bucky. Therefore, the image plate cassette and the film cassette repeat mount within the bucky and detachment from the bucky whenever radiography is performed, thereby providing user's inconvenience.

DISCLOSURE

Technical Problem

Therefore, the present invention has been made in view of the above problems, and it is an object of the present invention to provide a digital radiography system having electronic cassettes which are detachably mounted on bucky trays and are portable.

It is another object of the present invention to provide a digital radiography system which allows a plurality of electronic cassettes to be used in a plurality of digital radiography systems in real time.

It is another object of the present invention to provide a digital radiography system which prevents confusion generated when a plurality of electronic cassettes are used, and maximizes radiography automation.

It is another object of the present invention to provide a digital radiography system in which bucky trays have a structure being capable of firmly and stably fixing electronic cassettes.

It is another object of the present invention to provide a digital radiography system in which bucky trays are provided with fixing devices to interchangeably use image plate cassettes or film cassettes.

It is another object of the present invention to provide a digital radiography system having an ID reader which recognizes an ID of an electronic cassette mounted on a bucky tray and a mount state of the electronic cassette on the bucky tray.

It is another object of the present invention to provide a digital radiography system in which a bucky tray supplies power to an electronic cassette connected to a workstation wirelessly.

It is another object of the present invention to provide a digital radiography system which prevents X-ray generation and unnecessary increase in an amount of radiation exposed to a patient due to a mount error, a radiography position error, and a setting error of the electronic cassette.

It is another object of the present invention to provide a digital radiography system in which at least two depressed grooves are provided on the edge of an electronic cassette so as to stably and firmly fix the electronic cassette to a bucky tray.

It is another object of the present invention to provide a digital radiography system which displays a channel of an electronic cassette connected to a workstation.

It is another object of the present invention to provide a digital radiography system which identifies a plurality of electronic cassettes using ID chips (barcodes).

It is another object of the present invention to provide a digital radiography system which performs radiography using an electronic cassette selected from among a plurality of electronic cassettes through electronic cassette selection switches of the electronic cassettes.

It is a further object of the present invention to provide a digital radiography system in which a bucky tray or a storage device supplies operating power to an electronic cassette.

Technical Solution

In accordance with an aspect of the present invention, the above and other objects can be accomplished by the provision of a digital radiography system including bucky trays on which a plurality of portable electronic cassettes is detachably mounted, and a workstation connected with the bucky trays through communication to identify the plurality of portable electronic cassettes and to control pre-processing files of the identified electronic cassettes.

The workstation may include a pre-processing unit to apply the pre-processing files corresponding to the plurality of electronic cassettes to the plurality of electronic cassettes, and a communication and image acquisition unit provided with channels to communicate with the plurality of electronic cassettes to acquire radiography images.

In the digital radiography system, the workstation may transmit the pre processing files of the electronic cassettes mounted on the bucky trays to other workstations provided in other digital radiography systems through the network and a portable storage device.

Each bucky tray may have a function of identifying an electronic cassette mounted thereon in order to prevent confusion generated when the plurality of electronic cassettes is used in the digital radiography system.

Each bucky tray may include safety fixing devices to prevent damage to the electronic cassette due to operator's carelessness.

Each safety fixing devices may include a sensor to recognize the normal mount state of the electronic cassette.

Each bucky tray may further include two portable fixing devices to cause the electronic cassette to coincide with a central vertical line.

Each portable fixing device may include a sensor to recognize the mount state of the electronic cassette.

Each portable fixing device may further include a protruding portion to firmly and stably fix the electronic cassette.

Each bucky tray may further include channel display units to display a channel of the mounted electronic cassette.

Each bucky tray may further include position display units to identify a kind of the mounted electronic cassette or a mounted image plate cassette or film cassette and to display a central horizontal line according to the kind and size of the cassette.

Each bucky tray may further include a code reader to read an identification code provided on the electronic cassette.

Each bucky tray may further include a power supply unit to supply power to the electronic cassette.

The digital radiography system in accordance with the present invention may prevent increase in an amount of radiation exposed to a patient caused by a radiography mistake due a mount error, a radiography position error, and a setting error of the electronic cassette.

Each electronic cassette may include a channel display unit to display a channel connected to the workstation.

Each electronic cassette may further include at least one identification code to identify the electronic cassette.

Each electronic cassette may further include an electronic cassette selection switch to identify the electronic cassette on which radiography is to be carried out.

Each electronic cassette may further include a power terminal to receive power supplied from the bucky tray.

Advantageous Effects

A digital radiography system in accordance with the present invention uses electronic cassettes in replace of fixed flat panel detectors, and thus is capable of employing various radiography techniques, minimizes an amount of radiation exposed to a patient, prevents unnecessary enlargement of an image, and allows a radiography position minimizing movement of an emergent patient or a serious patent to be freely selected.

Further, the digital radiography system allows the electronic cassettes to be interchangeably mounted on and detached from other digital radiography systems in real time by an operator, thereby maximizing efficiency in use of the expensive electronic cassettes at the minimum number of the electronic cassettes.

Further, each of the electronic cassettes includes channel display units, thereby minimizing operator's confusion due to use of the same electronic cassette.

Further, each of the electronic cassettes includes an electronic cassette selection switch, thereby allowing one electronic cassette to be selected from among the plural electronic cassettes used in the digital radiography system.

Further, since a large area electronic cassette, a small area electronic cassette, an image plate cassette, and a film cassette may be freely selectively mounted on a bucky tray, and thus efficiency in use of the digital radiography system is increased.

Further, an ID chip of the electronic cassette mounted on the bucky tray is read and a mount state of the electronic cassette is recognized in real time so as to maximize automation in radiography, and if the mount state of the electronic cassette is not normal, generation of X-rays is prevented and thus unnecessary amount of radiation exposed to a patient is reduced.

Moreover, since the bucky tray supplies power to the electronic cassette, the capacity of a storage battery of the electronic cassette is reduced and thus the electronic cassette is light-weighted, and the operator does not need to connect the electronic cassette to a power supply device of the electronic cassette in order to recharge the electronic cassette, thereby providing convenience.

DESCRIPTION OF DRAWINGS

The above and other objects, features and other advantages of the present invention will be more clearly understood from the following detailed description taken in conjunction with the accompanying drawings, in which:

FIG. 11a is a view illustrating a state in which the large area electronic cassette is vertically mounted on the bucky tray in the reverse direction, FIG. 11b is a view illustrating a state in which the large area electronic cassette is vertically mounted on the bucky tray in the forward direction;

FIG. 13a is a view illustrating a process of mounting the large area electronic cassette on the bucky tray, FIG. 13b is a view illustrating a state in which the large area electronic cassette is mounted on the bucky tray; and FIG. 13c is a longitudinal-sectional of the large area electronic cassette mounted on the bucky tray;

BEST MODE

Now, a preferred embodiment of the present invention will be described in detail with reference to the annexed drawings. In the following description of the present invention, a detailed description of known functions and configurations incorporated herein will be omitted when it may make the subject matter of the present invention rather unclear.

Figure 1:
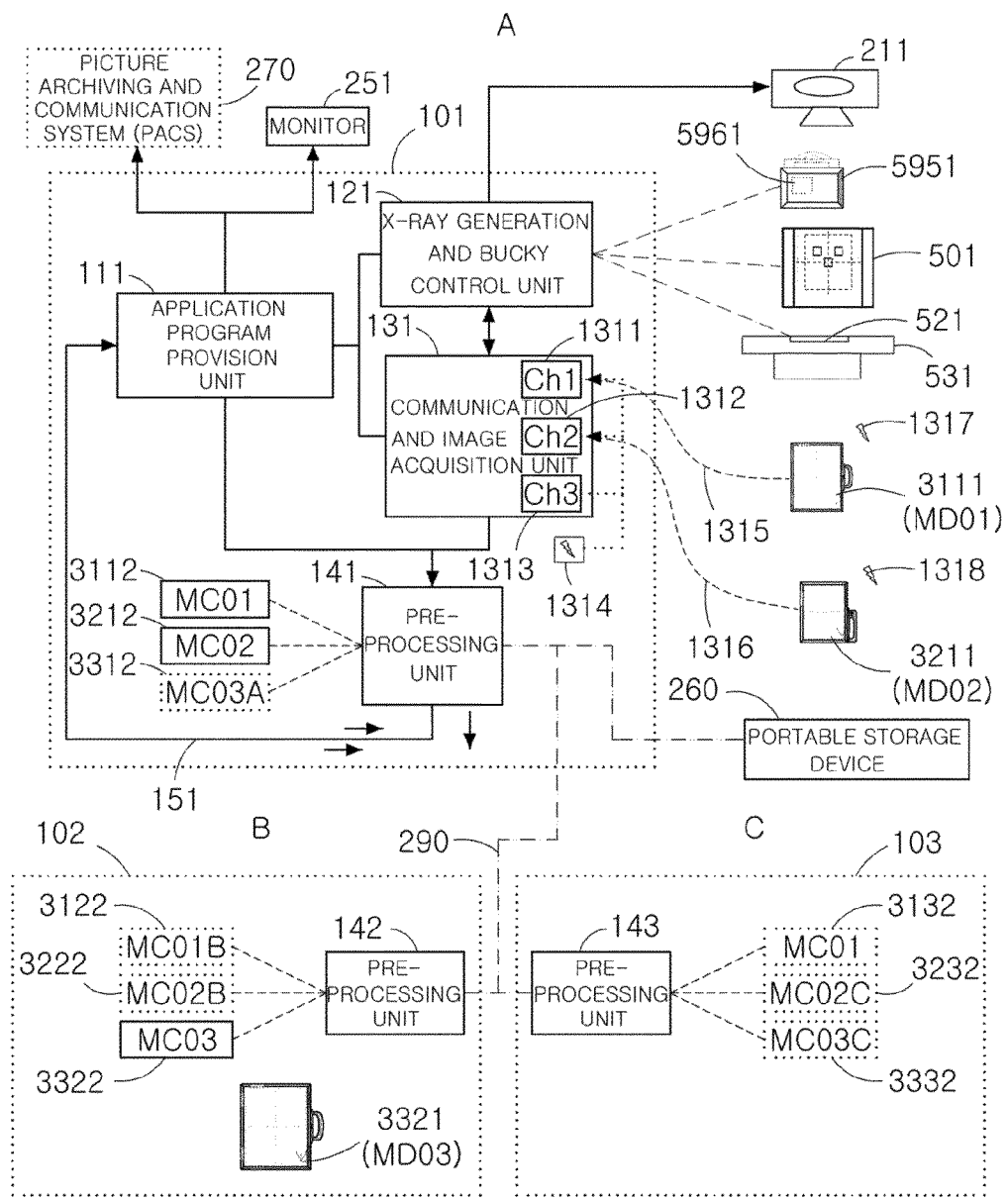
FIG. 1 is a view illustrating a concept of a digital radiography system using electronic cassettes in accordance with the present invention.

FIG. 1 is a view illustrating a concept of a digital radiography system A using electronic cassettes in accordance with the present invention. The digital radiography system includes a workstation 101, a monitor 251, an X-ray generation and bucky control unit 121, a table 531, a table bucky 521, a stand bucky 501, an electronic cassette storage device 5951, and electronic cassettes 3111 and 3211.

The workstation 101 includes the X-ray generation and bucky control unit 121, a communication and image acquisition unit 131, a pre-processing unit 141, and an application program provision unit 111. The workstation 101 generally controls the digital radiography system.

The X-ray generation and bucky control unit 121 controls an X-ray generator 211 and the buckies 501 and 521, and is connected with the application program provision unit 111 and the communication and image acquisition unit 131.

The communication and image acquisition unit 131 performs a series of processes of determining channels of the electronic cassettes connected with the workstation 101, achieving multi-control of the connected electronic cassettes, and acquiring images. Here, the number of the channels connected with the workstation 101 is two or more. Particularly, communication methods for connecting the electronic cassettes with the workstation 101 may be wire communication methods 1315 and 1316 or wireless communication methods 1317 and 1318.

The pre-processing unit 141 serves to search and apply correction files 3122, 3222, 3322, 3132, 3232, and 3332 of a second digital radiography system B including a pre-processing unit 142 and a portable digital radiography system C including a pre-processing unit 143 as well as serves to manage and apply connection files 3112, 3212, and 3312 corresponding to portable flat panel detectors 3111, 3211, and 3321.

The application program provision unit 111 serves to search and apply patient and inspection data through a Picture Archiving and Communication System (PACS) 270 or to directly input the patient and inspection data by hand, to generate an image 1112 optimized through post-processing 1111 based on a clean image CI01 through pre-processing, to store the optimized image in a database, and to transmit the optimized image to the PACS 270.

In the above patient and inspection data, since inspection methods to precisely perform inspection and set of equipment are various and complicated, there is a great diagnostic value difference between acquired images according to expertness of operators. Therefore, in order to acquire images at the same quality at all times, the equipment needs to be automatically set according to patient and inspection data. Therefore, the application program provision unit 111 serves to automatically set radiography conditions, to automatically set the bucky, and to automatically set the detector, and has an overall control function, such as display of the mount state of the electronic cassettes and warning message generation due to a setting error, using a graphic user interface.

Figure 2:
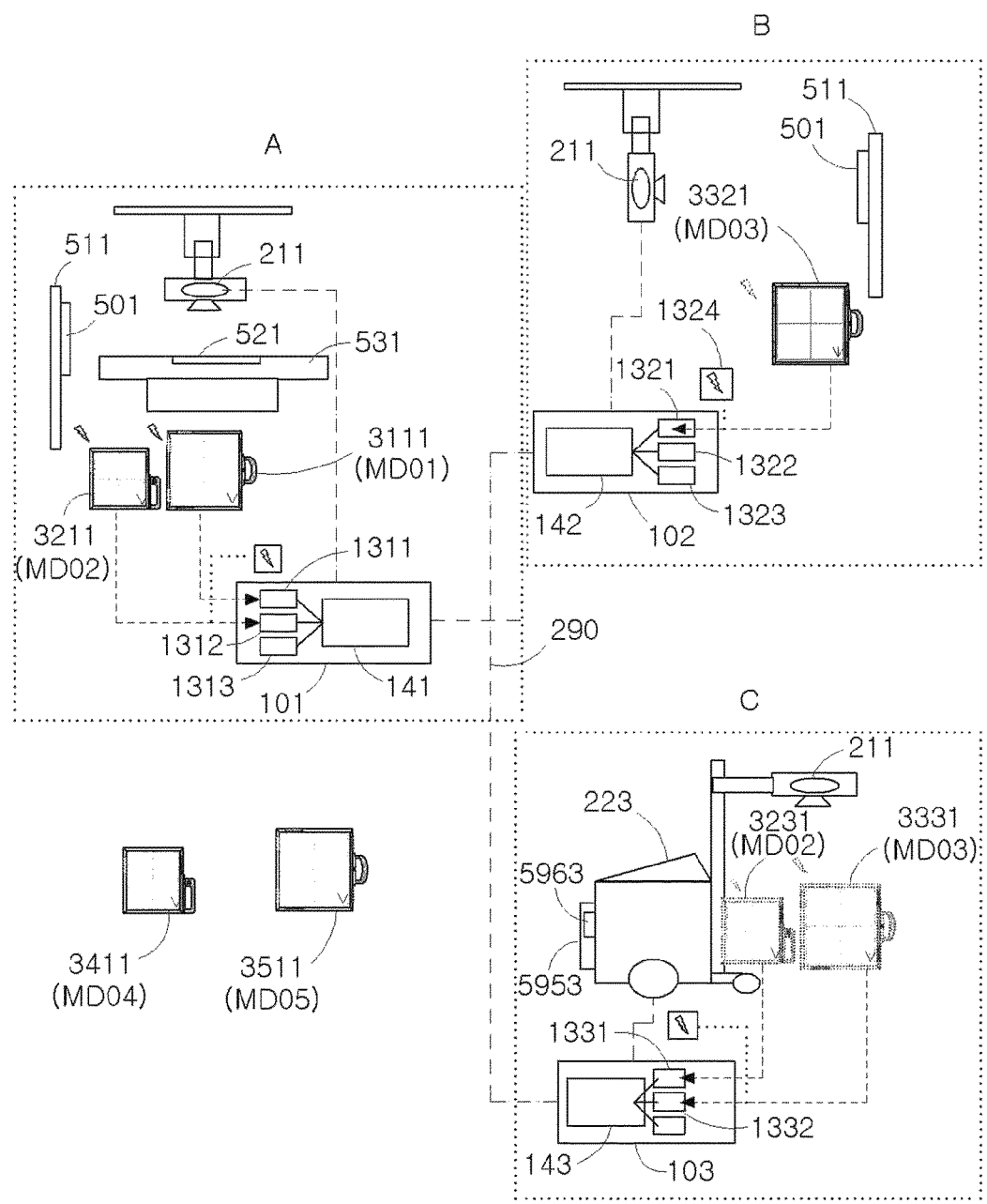
FIG. 2 is a view illustrating utilization of the digital radiography system using electronic cassettes in accordance with the present invention.

FIG. 2 illustrates utilization states of the electronic cassettes in accordance with the present invention. The first digital radiography system A, the second digital radiography system B, and the portable digital radiography system C, i.e., three digital radiography systems, use three electronic cassettes. The first digital radiography system A uses two electronic cassettes 3111 and 3211.

The two electronic cassettes 3111 and 3211 used in the first digital radiography system A are divided into two types of cassette, i.e., a large area electronic cassette 3111 and a small area electronic cassette 3211. The large area electronic cassettes 3111 and 3321 have a detection area of 14×17 inches, and the small area electronic cassette 3211 has a detection area of 10×12 inches. Since kinds and methods of radiography are various, the large and small area electronic cassettes are divisionally used. That is, the large area electronic cassette is used in radiography of the abdomen, the chest, or the spine of a patient, and the small area electronic cassette is used in radiography of the legs and arms or a part of the body of the patient, which is bent or requires special radiography, thereby increasing efficiency in radiography.

The second digital radiography system B is a radiography system only for the chest. Such a radiography system is used in radiography of the chest of an inpatient, an outpatient, or a person undergoing a medical checkup. Inspection using the second digital radiography system B is mostly carried out in the morning, and is scarcely carried out in the afternoon and night. Therefore, in the afternoon and night when the inspection using the second digital radiography system is scarcely carried out, the electronic cassette 3321 of the second digital radiography system B may be used as being loaded on the third channel Ch3 1313 of the first digital radiography system A or being loaded on the portable digital radiography system C.

The portable digital radiography system C is moved to a patient's room to perform radiography of the body of a patient if the patient in an emergency room or an intensive care unit cannot move to a radiography room. In case of such a radiography system, inspection is frequently required but an inspection quantity is not great. When the electronic cassette 3111, 3211, or 3321 is unloaded from the first digital radiography system and is then loaded on the portable digital radiography system C, the inspection using the portable digital radiography system C may be performed in the emergency room or the intensive care unit. When the inspection has been completed, the electronic cassette 3111, 3211, or 3321 is unloaded from the portable digital radiography system C, and is again loaded on the first digital radiography system.

The three digital radiography systems A, B, and C uses the three electronic cassettes in such a manner, thereby being capable of increasing utility of expensive portable flat panel detectors. If items of inspections are simple and all the inspections are easily achieved using the large area portable flat panel detectors, the small area portable flat panel detector is not required. In this case, the three digital radiography systems A, B, and C may be used only with the two large area electronic cassettes 3111 and 3321.

Figure 3:
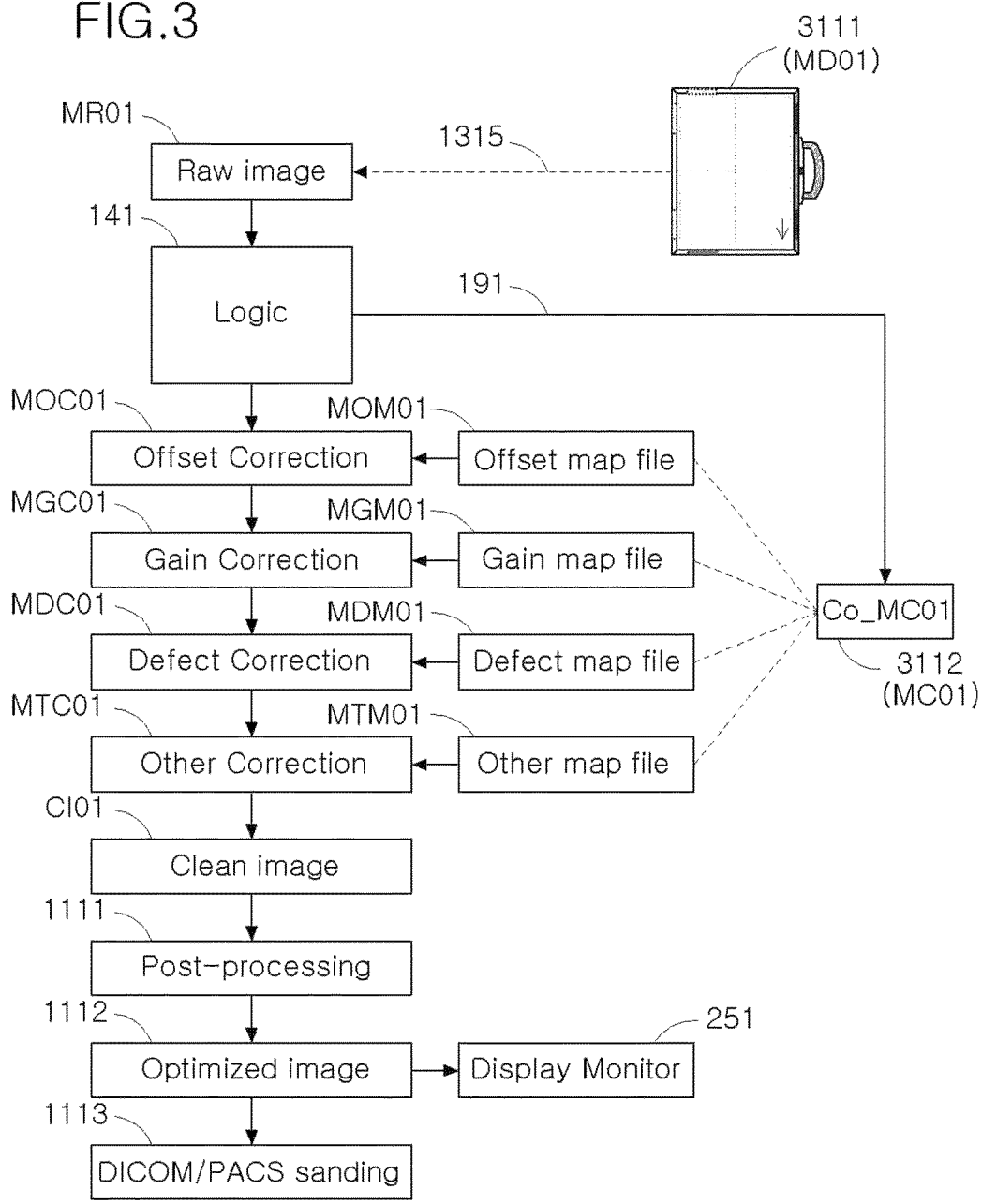
FIG. 3 is a block diagram illustrating image pre-processing of an electronic cassette in accordance with the present invention.

FIG. 3 is a block diagram illustrating image pre-processing of the electronic cassette in accordance with the present invention. The electronic cassette has defective pixels in aspect of characteristics thereof, and requires, in order to acquire a clean and precise image, correction files MC01 3112 to correct the defective pixels. The correction files are obtained through a process called calibration 191 of the electronic cassette, and calibration 191 is achieved by a general method provided by an electronic cassette manufacturing company. Here, an offset map file MOM01, a gain map file MGM01, a defect map file MDM01, and an other map file MTM01 are generated. These correction files are necessary to convert a raw image MR01 into a clean image CI01, and the collection files MC01 3112 need to be updated in real time. Because characteristics of offset and defective pixels of the electronic cassette are changed in real time according to the number of times of radiography, an amount of radiation, and a change of surrounding temperature. Therefore, in order to acquire the optimum clean image CI01, the correction files MC01 3112 must be updated in real time. The pre-processing unit 141 serves to update the correction files MC01 3112.

In order to use the electronic cassette 3111 of the first digital radiography system A in any other system B or C, the following two requirements must be satisfied.

First, the correction files MC01 3112 of the electronic cassette MD01 3111 having the correct serial numbers must be applied to any other system B or C. Since offset and defective pixels in the correction files are changed in real time according to the state of the electronic cassette, and the latest updated correction files must be applied.

Second, power must be continuously supplied to the electronic cassette. When power is cut off and is again supplied to the electronic cassette after a designated time, the offset of the electronic cassette 3111 is rapidly changed. The offset and defective pixels generated from the electronic cassette at this time considerably differ from the offset map file MOC01 and the defect map file MDC01 stored in the pre-processing units 141, 142, and 143. Therefore, if the raw image MR01 is acquired and pre-processing is performed through the pre-processing unit at this time, acquisition of the optimum clean image CI01 is not assured.

The workstations of the digital radiography systems A, B, and C respectively include the pre-processing units 141, 142, and 143 to apply pre-processing files of plural electronic cassettes to plural digital radiography systems, and the electronic cassettes 3111 and 3211 respectively include storage batteries 3048 and 3248. In order to separate the electronic cassette 3111 from the first digital radiography system A and then load the electronic cassette 3111 on the second digital radiography system B, the above two requirements must be satisfied. Since the logics 141, 142, and 143 possess the pre-processing files in common through a network, when the electronic cassette 3111 is loaded on the second digital radiography system B, the logic 142 of the second digital radiography system B searches the pre-processing file 3112 of the electronic cassette 3111, which was applied the latest, in the logic 141 of the first digital radiography system A, and applies the searched pre-processing file 3112 as the pre-processing file 3122 MC01B of the logic 142 of the second digital radiography system B. In such a method, the latest updated pre-processing file may be applied. Further, the storage battery 3048 of the electronic cassette 3111 prevents cutoff of power until the electronic cassette 3111 is unloaded from the first digital radiography system A and is then loaded on the second digital radiography system B.

Figure 4:
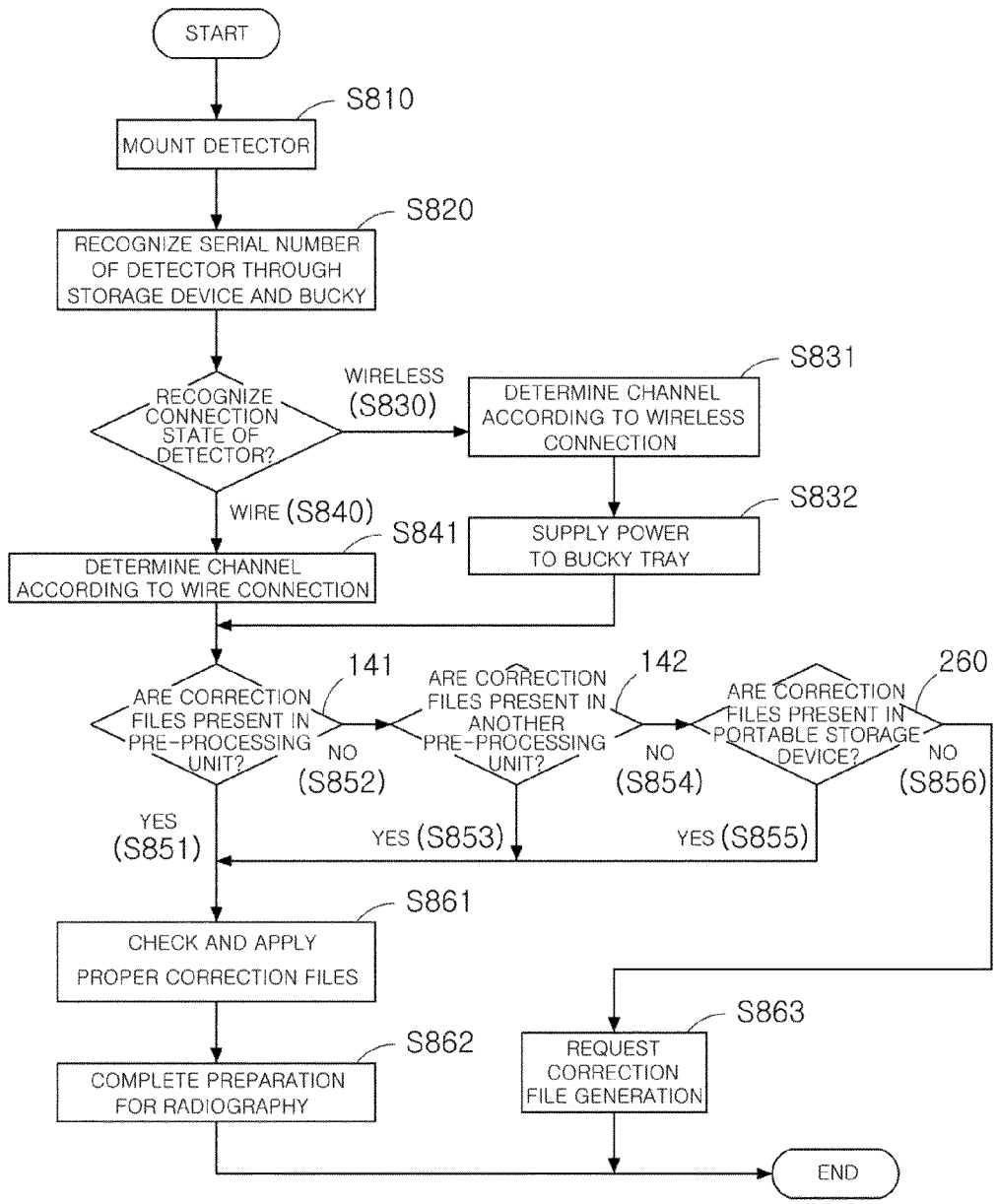
FIG. 4 is a flow chart illustrating loading the electronic cassette on the digital radiography system.

FIG. 4 illustrates a collection file searching process in accordance with the present invention. When the electronic cassette 3111 is mounted on the bucky 501 or 521 or the electronic cassette storage device 5951 or 5953 (operation S810), an ID chip reader 5061 mounted on a bucky tray 5000 or an ID chip reader 5961 or 5953 mounted on the electronic cassette storage device 5951 or 5953 recognizes a serial number of the electronic cassette 3111, stored in an electronic ID chip 651, 652, or 653 of the rear surface of the electronic cassette 3111 (operation S820), and transmits the recognized serial number to the X-ray generation and bucky control unit 121. Here, a barcode may be used instead of the electronic ID chip, and, when the barcode is used, a barcode reader is preferably used instead of the ID chip reader. Further, if other methods to identify the device other than the barcode is used, readers corresponding to the methods may be used. That is, the ID chip and the barcode may be referred to as identification codes, and equipment to read the identification codes may be referred to as a code reader.

The X-ray generation and bucky control unit 121 transmits the serial number of the electronic cassette to the communication and image acquisition unit 131 and the application program provision unit 111. The communication and image acquisition unit 131 checks a connection state of the electronic cassette 3111 to the workstation. If the electronic cassette 3111 is connected to the workstation by wire (operation S840), the channel Ch1, Ch2, or Ch3 is determined according to the wire communication method 1315 or 1316 (operation S833), and if the electronic cassette 3111 is connected to the workstation wirelessly (operation S830), the channel Ch1, Ch2, or Ch3 is automatically determined according to the wireless communication method 1314 (operation S831) and a power supply unit of the bucky tray supplies power to the electronic cassette.

The pre-processing unit 141 recognizes the channel 1311 of the electronic cassette 3111 connected to the workstation and the serial number MD01 of the electronic cassette 3111, and checks whether or not the correction files MC01 3112 corresponding thereto are present in the pre-processing unit 141. If the correction files MC01 3112 are present (operation S851), the correction files MC01 3112 are recognized and applied (operation S861), and a preparation for radiography is completed (operation S862). On the other hand, if the connection files MC01 3112 are not present in the system (operation S852), correction files MC01B 3122 or MC01C 3132 stored in the pre-processing unit 142 of another system or a portable storage device 260 are searched, and the latest applied correction files among these correction files are searched and applied (operation S861), and the preparation for radiography is completed (operation S862). However, if applicable correction files are not searched (operation S856), correction file generation is requested (operation S853), and then the process is terminated.

Figure 5:
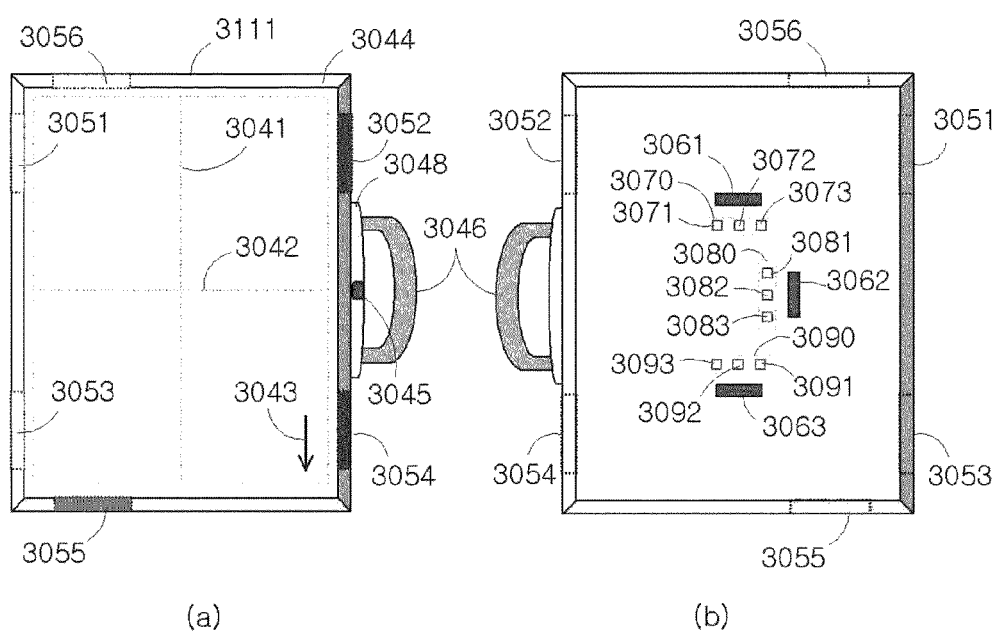
FIG. 5a is a front view of a large area electronic cassette.
FIG. 5b is a rear view of the large area electronic cassette.
Figure 6:
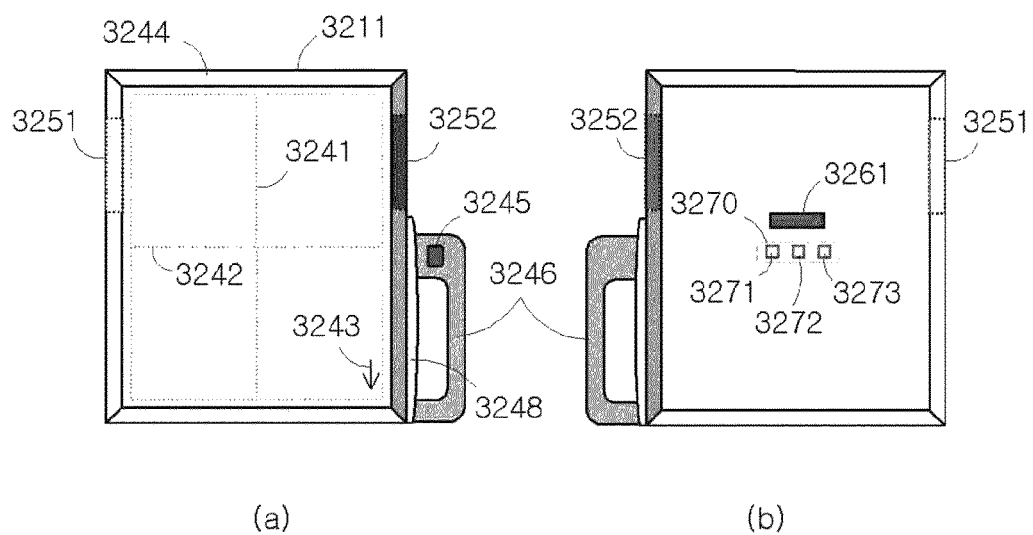
FIG. 6a is a front view of a small area electronic cassette.
FIG. 6b is a rear view of the small area electronic cassette.

FIG. 5 illustrates front and rear views of the large area electronic cassette 3111, and FIG. 6 illustrates front and rear views of the small area electronic cassette 3211. The large area electronic cassette has a detection area of 14×17 inches, and the small area electronic cassette has a detection area of 10×12 inches. The electronic cassettes (hereinafter, referred to as merely electronic cassettes if it is not necessary to divide the electronic cassettes into the large area electronic cassette and the small area electronic cassette) respectively include direction indicators 3043 and 3243, central vertical lines 3041 and 3241, and central horizontal lines 3042 and 3242 on front detection surfaces of the electronic cassettes, respectively include impact absorption parts 3044 and 3244 to absorb external impact and fixing grooves 3051~3056 and 3251, 3252 to safely and firmly fix the electronic cassettes to the bucky tray at the edges of the electronic cassettes. Further, the electronic cassettes respectively include handles 3046 and 3246 to provide convenience in carriage, the storage batteries 3048 to supply power, and channel display units 3045 and 3245 to display connected channels and preparation states of the electronic cassettes. The storage batteries 3048 and the channel display units 3045 and 3245 are provided around the handles 3046 and 3246. Here, the channel display units 3046 and 3246 respectively include electronic cassette selection switches 3045a and 3445a to select a specific electronic cassette from among the plural electronic cassettes. Further, the electronic cassettes respectively include electronic ID chips 3061~3063 and 3261 and power terminal units 3070, 3080, 3090 and 3270.

The direction indicator 3043 or 3243 of the portable flat panel detector serves to define the direction of an acquired image. When an image is acquired under the condition that the direction 711 of an arrow of the direction indicator 3043 or 3243 is set to the upward direction, a correct image 721 is acquired. The central vertical line 3041 or 3241 and the central horizontal line 3042 or 3242 serve to guide the center of the electronic cassette.

The six fixing groves 3051~3056 are formed at the edge of the large area electronic cassette, and serve to safely and firmly fix the electronic cassette to the bucky tray 5000.

Figure 7:
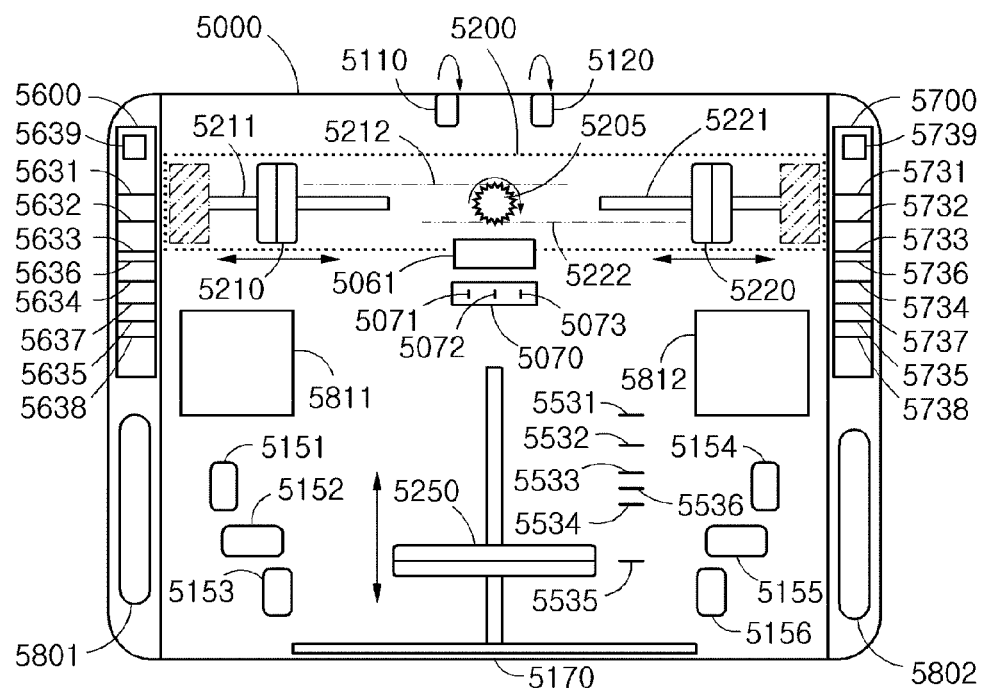
FIG. 7 is a view illustrating a structure of a bucky tray.
Figure 8:
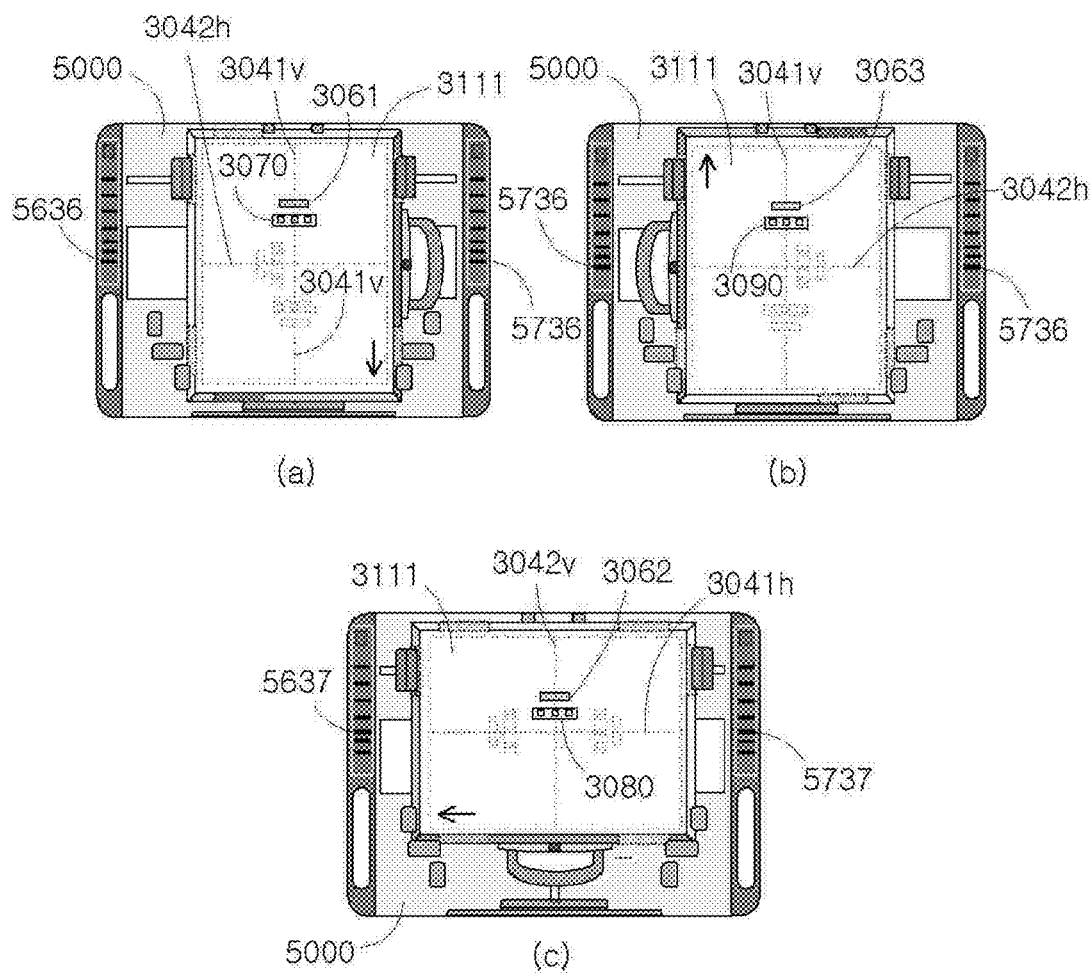
FIG. 8a is a view illustrating a state in which the large area electronic cassette is vertically mounted on the bucky tray in the reverse direction.
FIG. 8b is a view illustrating a state in which the large area electronic cassette is vertically mounted on the bucky tray in the forward direction.
FIG. 8c is a view illustrating a state in which the large area electronic cassette is horizontally mounted on the bucky tray in the reverse direction.

FIG. 7 is a view illustrating a detailed configuration of the bucky tray, and FIG. 8 illustrates various states in which the large area electronic cassette is mounted on the bucky tray. In order to firmly fix the large area electronic cassette in any mount state, the fixing grooves of the large area electronic cassette include two fixing grooves 3051 and 3052 located at the left and right sides of the upper end and two fixing grooves 3053 and 3054 located at the left and right sides of the lower end with respect to the central horizontal line 3041 and two fixing grooves 3055 and 3056 located at the upper and lower ends of the left side with respect to the central vertical line 3042. The two fixing grooves 3051 and 3052 located at the left and right sides of the upper end of the large area electronic cassette 3111 are engaged with fixing devices 5230 and 5240 when the large area electronic cassette 3111 is vertically mounted on the fixing device in the reverse direction (FIG. 11(a)). The two fixing grooves 3053 and 3054 located at the left and right sides of the lower end of the large area electronic cassette 3111 are engaged with the fixing devices 5230 and 5240 when the large area electronic cassette 3111 is vertically mounted on the fixing device in the forward direction (FIG. 11(b)). The two fixing grooves 3055 and 3056 located at the upper and lower ends of the left side are engaged with the fixing devices 5230 and 5240 when the large area electronic cassette 3111 is horizontally mounted on the fixing device in the forward direction or the reverse direction (FIG. 8(c)). A fixing member 3031 has the same thickness as the thickness (about 10 m) of the conventional image plate cassette and the film cassette.

The small area electronic cassette 3211 includes two fixing grooves 3251 and 3252 at the edge thereof. The fixing grooves 3251 and 5252 serve to safely and firmly fix the small area electronic cassette 3211 to the bucky tray.

Figure 9:
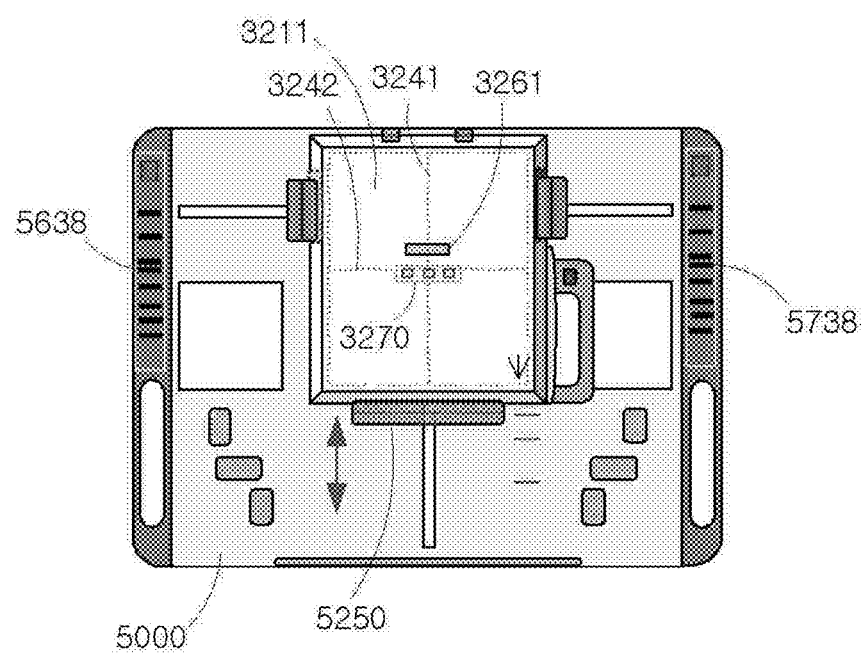
FIG. 9 is a view illustrating a state in which the small area electronic cassette is mounted on the bucky tray.

FIG. 9 is a view illustrating a state in which the small area electronic cassette is mounted on the bucky tray. In order to firmly fix the small area electronic cassette to the bucky tray, the small area electronic cassette includes two fixing groves 3251 and 3252 located at the left and right sides of the upper end thereof with respect to the central horizontal line 3242.

The small area electronic cassette may include only the two fixing grooves differing from the large area detector. The small area electronic cassette has a small size and does not have a limit in an inspection method thereof according to mount forms on the bucky tray 5000, and thus may be fixed to the bucky tray in only one form.

The electronic cassettes 3111 and 3211 respectively include the storage batteries 3048 and 3248 to supply power, and thus the storage batteries 3048 and 3248 supply operating power to the electronic cassettes 3111 and 3211.

When the electronic cassettes are connected to the workstation 101 wirelessly 1314, power is supplied to the electronic cassettes by the storage battery 3048 and 3248. Charging power of the storage batteries is supplied by a power supply unit 5061 of the bucky tray 5000 and power supply units 5961 and 5963 of the electronic cassette storage devices 5951 and 5953. The electronic cassettes receive power supplied by the bucky tray, and thus, when the electronic cassettes are mounted on the bucky and inspection is continuously performed, restriction on continuous inspection due to limit of the capacity of the storage battery does not occur.

When the electronic cassettes are connected to the workstation 101 by wire 1315 are 1316, the electronic cassettes receive power supplied by wire. The electronic cassettes does not directly use the power supplied by wire as operating power, but uses the supplied power as charging power of the storage batteries 3048. This serves to prevent temporary operating power supply cut off generated when the connection of the electronic cassette to the workstation 101 by wire is released so as to interchangeably load the electronic cassette on another digital radiography device B or C, and to prevent an operation error and power supply cut off due to poor contact at a connection portion of a wire.

The channel display units 3045 and 3245 of the electronic cassettes display channels connected to the workstation 101 at present. When two or more electronic cassettes are loaded on the digital radiography system and used, a user must precisely distinguish the electronic cassette selected to acquire an image. If the electronic cassettes are not distinguished, the user may perform a preparation for inspection to the first electronic cassette 3111 but image acquisition may be carried out on the second electronic cassette 3211. This causes a patient to be exposed to radiation without acquiring a precise image. In order to prevent such a mistake, the user must easily and conveniently distinguish the electronic cassettes. As a method of distinguishing the electronic cassettes, the electronic cassettes respectively display channels of the electronic cassettes which are connected to the workstation 101 at present. The channel display units 3045 and 3245 respectively include the electronic cassette selection switches 3045a and 3445a. When the user closes the electronic cassette selection switch for about 2 seconds, the electronic cassette selection switch transmits the fact that the corresponding electronic cassette is used in radiography to the workstation. When the user uses the plural electronic cassettes in the radiography room, the user must precisely distinguish the respective electronic cassettes. However, if the user radiographs an emergency patient or a serious patient, the user may make a mistake in radiography until the user is skilled. In order to prevent such a mistake, the user selects one from among the electronic cassette selection switches and confirms the selected electronic cassette selection switch during positioning the patient, and thus precisely distinguishes the electronic cassette used in radiography from other electronic cassettes and informs the workstation of the electronic cassette used in radiography so as to acquire an image, thereby minimizing the mistake in radiography. That is, the electronic cassette selection switches have a function that an electronic cassette selected from among plural electronic cassettes is used in radiography so as to achieve precise radiography.

The channel displays 3045 display inspection preparation states of the electronic cassettes 3111 and 3211 as well as display the channels of the electronic cassettes 3111 and 3211. The channel displays 3045 and 3245 are turned off when channels of the electronic cassettes 3111 and 3211 are not connected to the workstation of the digital radiography system, are blinking in an inspection standby state when the channels of the electronic cassettes 3111 and 3211 are connected to the workstation and correction files are searched and applied, and are continuously turned on when the corresponding channels for inspection are selected and inspection preparation states are completed, thereby allowing the user to know the preparation states of the electronic cassettes.

The application program provision unit 111 defines channels of the electronic cassettes 3111 and 3211, and displays the channels on the channel displays 3045 and 3245 of the electronic cassettes, channel displays 5639 and 5739 of the bucky tray, and the display monitor 251. In channel display, the first channel is displayed in blue, the second channel is displayed in green, and the third channel is displayed in yellow so as to increase readability, and if additional channels are required, the channels and colors corresponding to the channels are defined separately.

The electronic cassettes include the ID chips 3061, 3062, 3063 and 3261 on the rear surfaces thereof. The ID chips store serial numbers and position data of the electronic cassettes. The ID chips are used to recognize the electronic cassettes in the bucky tray or the storage devices.

If plural electronic cassettes are used in the digital radiography system, the user performs bucky selection (selection of the stand bucky, selection of the table bucky, or nonuse of any bucky) according to the inspection purpose, and selects the electronic cassette which is desired to be used. If the user selects the stand bucky for inspection and then selects the electronic cassette mounted on the table bucky, X-rays are irradiated onto the stand bucky and an image on the electronic cassette mounted on the table bucky is acquired, thereby causing an inspection mistake. If the electronic cassette mounted on the stand bucky can be recognized and the connected channel of the electronic cassette can be recognized, the electronic cassette mounted on the stand bucky is automatically selected through selection of the stand bucky, thereby preventing the above mistake.

In order to recognize the electronic cassettes mounted on the buckies 501 and 521 and the storage devices 5951 and 5953, the buckies and the storage devices include the ID chip readers 5061, 5961, and 5963. When the small area electronic cassette 3211 is mounted on the stand bucky 501, the ID chip reader 5061 reads the serial number of the ID chip 3261 of the mounted small area electronic cassette 3211 and transmits the serial number to the X-ray generation and bucky control unit 121, the X-ray generation and bucky control unit transmits the serial number to the application program provision unit 111, the application program provision unit requests the communication and image acquisition unit 131 to give data corresponding to the serial number, the communication and image acquisition unit checks channel data 1312 of the electronic cassette connected to the serial number and transmits the channel data to the application program provision unit, the application program provision unit records the channel data and transmits the channel data to the X-ray generation and bucky control unit, and the X-ray generation and bucky control unit displays the channel data on the channel display devices 5639 and 5730. When the user selects the stand bucky 501, the application program provision unit refers to the recorded channel data, and automatically selects the electronic cassette 3211 mounted on the stand bucky.

The large area electronic cassette 3111 includes three ID chips. The large area electronic cassette has a large detection area of 14×17 inches, and the handle 3046 to provide convenience in carriage is located on one side of the large area electronic cassette.

The reason why the large area electronic cassette includes three ID chips is that the large area electronic cassette is mounted on the bucky tray in three forms.

FIG. 11 illustrate mount of the bucky tray 5000 within the stand bucky 501 in both directions, and FIG. 8 illustrates mount of the large area electronic cassette on the bucky tray. If the bucky tray is inserted into the right side of the stand bucky (FIG. 11(a)), the electronic cassette is difficult to be vertically mounted on the bucky tray in the forward direction (FIG. 8(b)). The reason is that the handle interferes with a bucky right case 554. Further, if the bucky tray is inserted into the left side of the stand bucky (FIG. 11(b)), the electronic cassette is difficult to be vertically mounted on the bucky tray in the reverse direction (FIG. 8(a)). The reason is that the handle interferes with a bucky left case 555. Therefore, the large area electronic cassette is mounted on the bucky tray, which can be inserted into bucky 501 in both directions, in three forms, as shown in FIG. 8. In case of any form of the three forms, the serial number of the electronic cassette mounted on the bucky tray must be recognized. For this purpose, the ID chips 3061, 3062, 3063 are located on the rear surface of the electronic cassette at positions corresponding to the ID chip reader 5061 of the bucky tray. If the electronic cassette is vertically mounted on the bucky tray in the reverse direction (FIG. 8(a)), the upper ID chip 3061 corresponds to the ID chip reader 5061, if the electronic cassette is vertically mounted on the bucky tray in the forward direction (FIG. 8(b)), the lower ID chip 3063 corresponds to the ID chip reader 5061, and if the electronic cassette is horizontally mounted on the bucky tray (FIG. 8(c)), the middle ID chip 3062 corresponds to the ID chip reader 5061.

The three ID chips may define central horizontal line positions 5637, 5638, 5737, and 5738 of the mounted large area electronic cassette 3111. Mount of the large area electronic cassette 3111 on the bucky tray 5000 is divided into vertical mount (FIGS. 8(a) and 8(b)) and horizontal mount (FIG. 8(c)). Coincidence between the central horizontal line positions 5637, 5737 or 5638, 5738 and a central horizontal line 3041h or 3042h of the electronic cassette is varied according to these mount forms. When the electronic cassette is vertically mounted on the bucky tray, the upper ID chip 3061 or the lower ID chip 3063 of the electronic cassette corresponds to the ID chip reader 5061, the correspondence is transmitted to the X-ray generation and bucky control unit 121, and the X-ray generation and bucky control unit 121 causes position displays of the bucky tray 5100 to indicate the third scale lines 5638 and 5738 for the electronic cassette. This means that the central horizontal line 3042*h* of the electronic cassette coincides with the third scale lines 5638 and 5738 for the electronic cassette of the position displays of the bucky tray 5000. When the electronic cassette is horizontally mounted on the bucky tray, the middle ID chip 3062 of the electronic cassette corresponds to the ID chip reader 5061, the correspondence is transmitted to the X-ray generation and bucky control unit 121, and the X-ray generation and bucky control unit 121 causes the position displays of the bucky tray 5000 to indicate the second scale lines 5637 and 5737 for the electronic cassette. This means that the central horizontal line 3041*h* of the electronic cassette coincides with the second scale lines 5638 and 5738 for the electronic cassette of the position displays of the bucky tray 5000. Further, the indication of the second scale lines for the electronic cassette and the third scale lines for the electronic cassette mean that the large area electronic cassette is mounted within the bucky.

The small area electronic cassette 3211 includes one ID chip. The small area electronic cassette has a relatively small detection area of 10×12 inches, and the handle 3246 to provide convenience in carriage is located on one side of the small area electronic cassette.

The reason why the small area electronic cassette includes one ID chip is that the small area electronic cassette is mounted on the bucky tray only in one form, as shown in FIG. 9, and thus requires only one ID chip corresponding to the ID chip reader.

FIG. 9 illustrates the central horizontal line of the small area electronic cassette mounted within the bucky as being indicated at the first scale lines 5636 and 5736 for the electric cassette of the position displays. This means mount of the small area electronic cassette within the bucky, and the indication means that that the central horizontal line 3042*h* of the mounted small area electronic cassette coincides with the first scale lines 5636 and 5736 for the electronic cassette of the position displays. Further, the indication of the first scale lines for the electronic cassette means that the small area electronic cassette is mounted on the bucky tray.

The power terminal units 3070, 3080, 3090 and 3270 are located on the rear surfaces of the electronic cassettes. When the electronic cassettes are connected to the workstation wirelessly, the electronic cassettes receive power supplied through the power terminal units. As shown in FIG. 5(*b*), the large area electronic cassette 3111 includes three power terminal units 3070, 3080, and 3090 on the rear surface thereof. The power terminal units 3070, 3080, and 3090 are located just below the ID chips 3061, 3062, and 3063. The power terminal units 3070, 3080, and 3090 serve to receive power in all mount states of the electronic cassette, as shown in FIG. 8. Further, as shown in FIG. 6(*b*), the small area electronic cassette 3211 includes one power terminal unit 3270 on the rear surface thereof. The power terminal unit 3270 is located just below the ID chip 3261. The power terminal units 3070, 3080, 3090 and 3270 respectively include power terminals 3071, 3081, 3091 and 3271, ground terminals 3072, 3082, 3092 and 3272, and sensor terminals 3073, 3083, 3093 and 3273.

Figure 15:
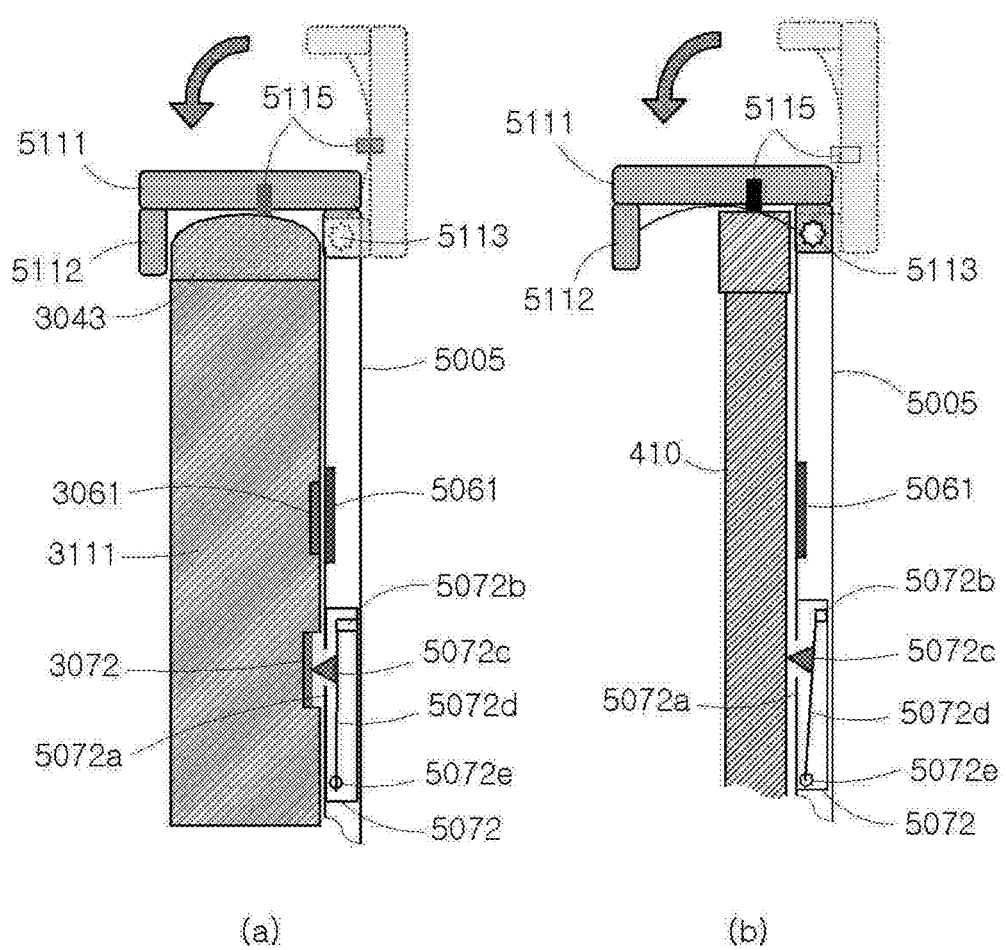
FIG. 15a is a longitudinal-sectional view of the large area electronic cassette fixed to a safety fixing device.
FIG. 15b is a longitudinal-sectional view of the image plate cassette fixed to the safety fixing device.

As shown in FIG. 15(*a*), the respective terminals of the power terminal units are depressed on the rear surfaces of the electronic cassettes, and respective terminals of a power supply unit 5070 corresponding to the respective terminals have the shape of a plug 5091. When the electronic cassette is normally mounted on the bucky tray and the storage device, the plug contacts the power terminal. The sensor 3073 checks whether or not the power terminal unit 3070 of the electronic cassette to normally contact the power supply unit 5070 of the bucky, and the bucky tray supplies power to the power terminal 3071 of the electronic cassette. A configuration and function of the power terminal unit 3070 are the same as those of other power terminal units 3080, 3090, and 3270.

Each of the buckies 501 and 521 is provided with an antiscatter moving grid 320 and an ion chamber 330, and the bucky tray 5000 located therebelow has a structure to fix the cassette 3111, 3211, 410, or 420 and then to be attached to and detached from the inside of the bucky, for example, has a structure, as shown in FIGS. 8, 9, 10, 11, 12, and 19. The antiscatter moving grid 320 removes scattered radiation generated from X-rays transmitted by a human body 910 so as to improve an image quality, and the ion chamber 330 serves to measure an amount of the transmitted X-rays and the measured amount is transmitted to the X-ray generator so as to control an amount of irradiated X-rays.

FIG. 7 is a view illustrating the bucky tray 5000 serving to mount the electronic cassette 3111 or 3211, the image plate cassette 410 and 420, or a film cassette thereon and to insert the cassette into the bucky. The bucky tray 5000 has a structure to attach and detach the cassette thereto and therefrom. The bucky tray 5000 includes display units 5600 and 5700 to display a channel and a mount state of the cassette, a fixing unit 5110~5222 to safely fix the cassette to the bucky tray 5000, a power supply unit 5070 to supply power of the electronic cassette, and an ID recognition unit 5060 to read the ID chip 3061~3063 or 3261 of the electronic cassette.

The display units 5600 and 5700 of the bucky tray 5000 to display the channel and the mount state of the cassette display a kind of the mounted cassette (the large area electronic cassette, the small area electronic cassette, the image plate cassette, or the film cassette), a connected channel of the electronic cassette and a preparation state thereof, a mount state of the cassette (the vertical mount or the horizontal mount), an insertion state of the bucky tray into the bucky, and so on.

The channel displays 5639 and 5739 of the display units 5600 and 5700 display a kind and a channel of the mounted cassette. When the cassette is mounted on the bucky tray 5000 and then the bucky tray is inserted into the bucky, the kind and the channel of the cassette mounted on the bucky tray cannot be checked, as shown in FIG. 13. In order to check the kind and the channel of the mounted cassette, the channel displays 5639 and 5739 display the channel displayed on the channel display 3045 or 3245 of the mounted electronic cassette 3111 or 3211 when the electronic cassette is mounted on the bucky tray, and are turned off when the image plate cassette is mounted on the bucky tray.

Figure 10:
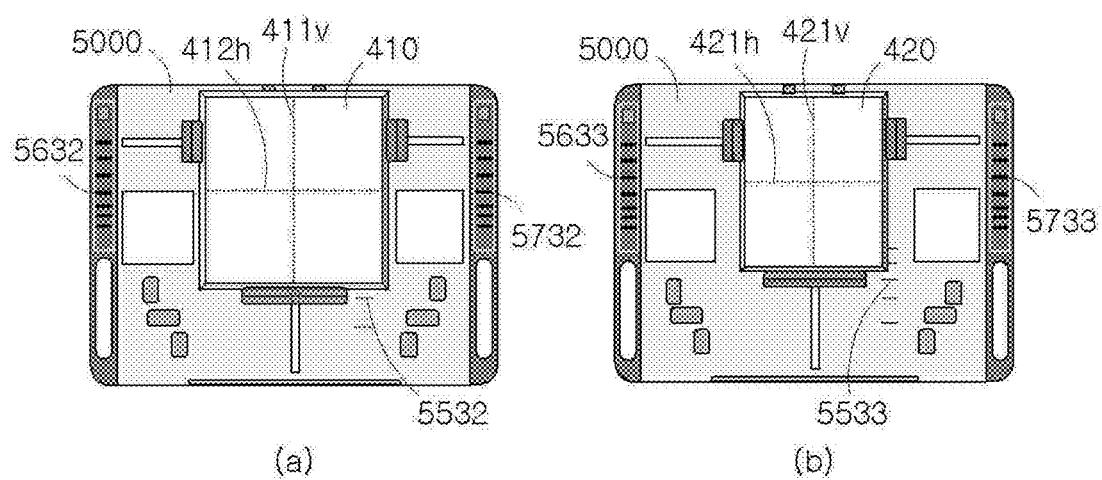
FIG. 10a is a view illustrating a state in which a 10×12 inch image plate cassette is vertically mounted on the bucky tray.
FIG. 10b is a view illustrating a state in which a 14×14 inch image plate cassette is vertically mounted on the bucky tray.

Position displays 5631~5638 and 5731~5738 of the display units 5630 and 5730 display the central horizontal line 3041*h*, 3042*h*, 3242*h*, 412*h*, or 421*h* of the mounted cassette and a mount state of the cassette, as shown in FIGS. 8, 9, and 10. The position displays are divided into electronic cassette central horizontal line displays to guide the central horizontal line 3041*h*, 3042*h*, and 3242*h* of the electronic cassette, and image plate cassette central horizontal line displays to guide the central horizontal lines 412*h* or 421*h* of the image plate cassette. The electronic cassette central horizontal line displays 5636~5638 and 5736~5738 are displayed in green and the image plate cassette central horizontal line displays 5631~5635 and 5731~5735 are displayed in yellow so as to easily distinguish the electronic cassettes and the image plate cassettes.

Figure 12:
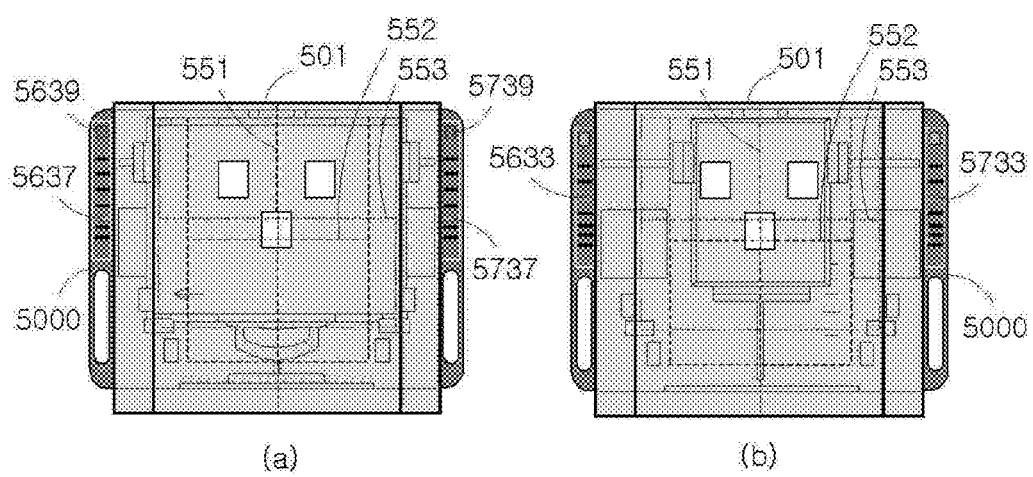
FIG. 12a is a view illustrating a state in which the large area electronic cassette is horizontally mounted within a bucky.
FIG. 12b is a view in which the 10×12 inch image plate cassette is horizontally mounted within the bucky.
Figure 14:
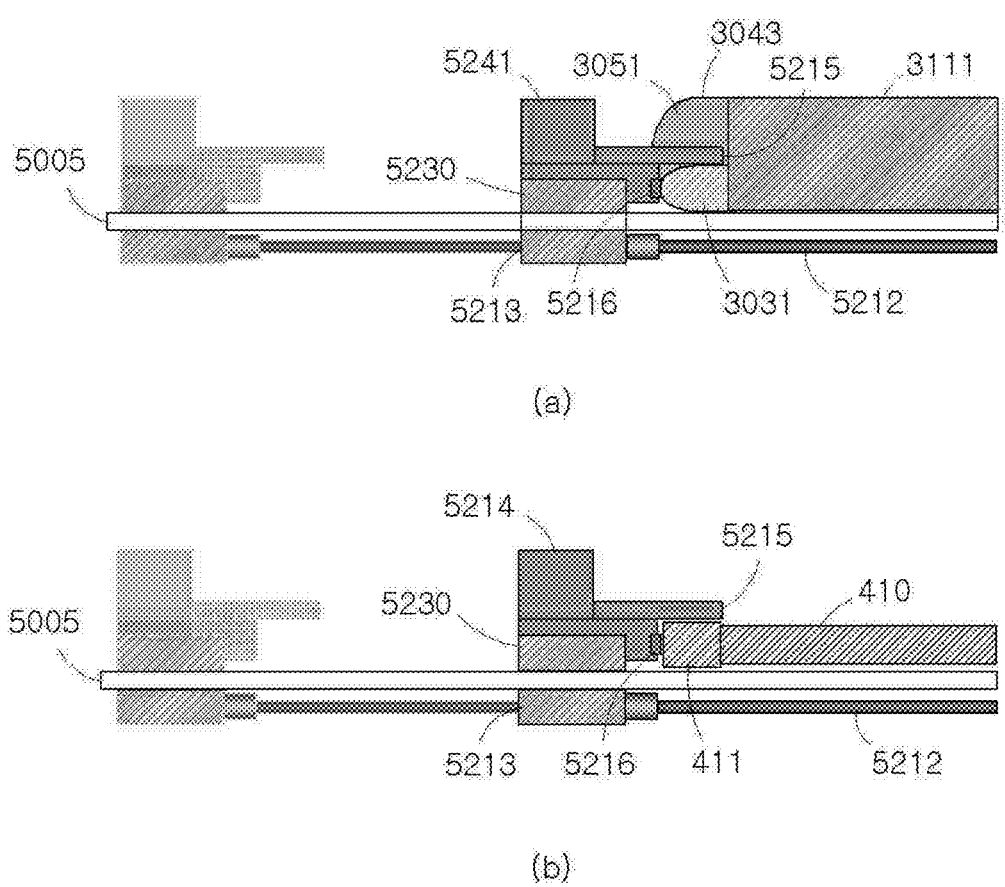
FIG. 14a is a longitudinal-sectional view of the large area electronic cassette fixed to a portable fixing device.
FIG. 14b is a longitudinal-sectional view of the image plate cassette fixed to the portable fixing device.

When the cassette is mounted on the bucky tray 5000 and the bucky tray is inserted into the bucky, the central horizontal line of the cassette mounted on the bucky tray and the mount state of the cassette cannot be checked, as shown in FIG. 12.

In order to check the central horizontal line and the mount state of the cassette, when the electronic cassette is mounted on the bucky tray 5000, the bucky tray recognizes the mount state of the electronic cassette 3111 or 3211 through the ID chip 3061, 3062, 3063 or 3261 on the rear surface of the electronic cassette and the ID chip reader of the bucky tray, and the electronic cassette central horizontal line displays 5636~5638 and 5736~5738 display the central horizontal line of the electronic cassette according to the mount state of the electronic cassette. FIGS. 8 and 9 illustrate embodiments in which the electronic cassette central horizontal line displays display the central horizontal lines of the electronic cassettes according to the mount states thereof. If the large area electronic cassette 3111 is vertically mounted on the bucky tray (FIGS. 8(*a*) and 8(*b*)), the third electronic cassette central horizontal line displays 5638 and 5738 are blinking, and are turned on when insertion of the bucky tray into the bucky has been normally completed. If the large area electronic cassette 3111 is horizontally mounted on the bucky tray (FIG. 8(*c*)), the second electronic cassette central horizontal line displays 5637 and 5737 are blinking, and are turned on when insertion of the bucky tray into the bucky has been normally completed. Further, if the small area electronic cassette 3211 is mounted on the bucky tray 5000 (FIG. 9), the first electronic cassette central horizontal line displays 5636 and 5736 are blinking, and are turned on when insertion of the bucky tray into the bucky has been normally completed.

FIG. 12(*a*) illustrates a state in which the electronic cassette is mounted within the bucky. Here, since the second electronic cassette central horizontal line displays 5637 and 5737 are turned on, it is understood that the portable flat panel detector is horizontally mounted within the bucky.

When the image plate cassette is mounted on the bucky tray 5000, the bucky tray recognizes a mount state of the image plate cassette through the position of a portable supporting and fixing device 5250, the image plate cassette central horizontal line displays 5631~5635 and 5731~5735 display the position of the central horizontal line 412*h* or 421*h* of the image plate cassette. The position of the central horizontal line 412*h* or 421*h* of the image plate cassette corresponds to the first image plate cassette central horizontal line displays 5631 and 5731 when the portable supporting and fixing device is located at a 8 inch position 5531, corresponds to the second image plate cassette central horizontal line displays 5632 and 5732 when the portable supporting and fixing device is located at a 10 inch position 5532, corresponds to the third image plate cassette central horizontal line displays 5633 and 5733 when the portable supporting and fixing device is located at a 12 inch position 5533, corresponds to the fourth image plate cassette central horizontal line displays 5634 and 5734 when the portable supporting and fixing device is located at a 14 inch position 5534, and corresponds to the fifth image plate cassette central horizontal line displays 5635 and 5735 when the portable supporting and fixing device is located at a 17 inch position 5535.

Kinds of image plate cassettes are divided into 8×10 inches, 10×12 inches, 14×14 inches, and 14×17 inches according to sizes of the image plate cassettes. An image plate mounted on the image plate cassette has a latent image when X-rays are irradiated onto the image plate, and is reused after the latent image is read by an image plate reader and is then erased. Therefore, the image plate cassette is repeatedly mounted on and detached from the bucky tray whenever inspection is performed, and a user frequently checks the mount state of the image plate cassette through the repetition of mount and detachment of the image plate cassette. However, the position of the central horizontal line of the mounted image plate cassette is varied according to the kind of the mounted image plate cassette, and thus is displayed through the image plate cassette central horizontal line displays.

FIG. 10 illustrates embodiments in which various image cassettes are mounted on the bucky tray. If a 14×14 inch image plate cassette 410 is mounted on the bucky tray (FIG. 10(*a*)), the fourth image plate cassette central horizontal line displays 5634 and 5734 are blinking, and are turned on when insertion of the bucky tray into the bucky has been normally completed. If a 10×12 inch image plate cassette is mounted on the bucky tray (FIG. 10(*b*)), the third image plate cassette central horizontal line displays 5633 and 5733 are blinking, and are turned on when insertion of the bucky tray into the bucky has been normally completed.

FIG. 12(*b*) illustrates a state in which the image plate cassette is mounted within the bucky. Here, since the third image plate cassette central horizontal line displays 5633 and 5733 are turned on in yellow, it is understood that the 10×12 inch image plate cassette is mounted within the bucky.

The fixing unit 5110~5160 and 5205~5260 of the bucky tray 5000 serves to safely and firmly fix the cassette to the center of the bucky tray, to transmit the fixed state of the cassette to the position display units of the bucky and the X-ray generation and bucky control unit, and to prevent the cassette from being detached from the bucky tray due to user's carelessness.

When radiography on the buck is performed (FIG. 12), a central vertical line 551 of the bucky 501 must coincide with the central vertical line 3041*v*, 3042*v*, 3241*v*, 411*v*, or 421*v* of the detector mounted on the bucky tray at all times. A user always sets the position of a patient with respect to the central vertical line 551 of the bucky 501 and then performs radiography. If the central vertical line of the cassette does not coincide with the central vertical line 551 of the bucky, a central vertical line of an acquired image leans to one side, and the acquired image is valueless in diagnosis.

The fixing unit of the bucky tray serves to stably and firmly fix the cassette to the center of the bucky. The fixing unit of the bucky tray includes portable fixing devices 5210 and 5220, the portable supporting and fixing device 5250, stationary fixing devices 5151~5156, and safety fixing devices 5110 and 5120.

The stationary fixing devices 5151~5156 serve as guide rails assisting stable mount of the large area electronic cassette 3111. FIG. 8 illustrates a process of mount the large area electronic cassette 3111 on the bucky tray 5000. The lower fixing bodies 5153 and 5156 serve as the guide rails when the large area electronic cassette is vertically mounted downward from above, the upper fixing bodies 5151 and 5154 serve as the guide rails when the large area electronic cassette is horizontally mounted downward from above, and the middle fixing bodies 5152 and 5155 serve as fixing supports when the large area electronic cassette is horizontally mounted downward from above (FIG. 8(*c*)). Contact surfaces of the fixing bodies corresponding to the large area electronic cassette are made of a material which is smooth and is not easily worn. The upper fixing bodies 5151 and 5154 and the lower fixing bodies 5153 and 5156 of the bucky tray 5000 include protrusions 5131 and 5161 bent suitable for the shape of the edge of the electronic cassette (FIG. 13(*c*)), and thus, when the large area electronic cassette is mounted on the bucky tray, the large area electronic cassette is not detached from the bucky tray unless the large area electronic cassette is lifted up. Thereby, detachment of the large area electronic cassette from the bucky tray of the stand bucky due to user's carelessness and damage to the large area electronic cassette caused by falling due to the detachment are prevented.

The portable supporting and fixing device 5250 supports the lower portion of the electronic cassette or the image plate cassette. The portable supporting and fixing device 5250 serves to set the position of the small area electronic cassette and fix the small area electronic cassette such that the small area electronic cassette coincides with the electronic cassette central horizontal line displays 5633 and 5733 and the fixing grooves 3251 and 3252 of the small area electronic cassette are smoothly engaged with the portable fixing bodies 5210 and 5220. Further, the portable supporting and fixing device 5250 serves to fix the image plate cassette so as to coincide with the image plate cassette central horizontal line displays and to transmit the position of the image plate cassette to the display units.

The safety fixing devices 5110 and 5120 include safety loops 5211, thereby preventing the detector mounted on the bucky tray from being detached from the bucky tray due to user's carelessness. Further, the safety fixing devices 5110 and 5120 include fixing sensors 5215, thereby transmitting an operating signal to a portable fixing device 5200. The safety fixing device 5110 includes a safety loop 5111, a fixing sensor 5115, a safety fixing protrusion 5112, and a fixing pin 5113.

When the detector is mounted on the bucky tray 5000, as shown in FIG. 15(*a*) and FIG. 15(*b*), the fixing pin 5112 of the safety fixing device 5110 fixes the safety loop 5111 to the bucky tray such that the safety fixing device 5110 is opened and closed, the safety fixing protrusion 5112 formed at the end of the safety loop prevents the cassette in the closed state of the safety fixing device from being easily separated from the bucky tray, and the fixing sensor 5115 provided in the direction of the fixing pin of the safety loop recognizes the mount state of the cassette 3111 or 410 on the bucky tray mounted on the bucky tray and transmits data regarding the mount state to the portable fixing device 5200. When the safety fixing devices are closed, the safety fixing devices are caught by the upper end of the cassette 3111 or 410 mounted on the bucky tray, and the fixing sensors of the safety fixing devices recognize that the cassette is mounted on the bucky tray, when a designated pressure or more is applied to regions between the cassette and the safety fixing devices, and transmit an operating command to the portable fixing device 5200 so as to fix the cassette. When the designated pressure or more is again applied to the safety fixing devices under the condition that the portable fixing devices fixes the cassette, the operating command is transmitted to the portable fixing device so as to release fixation of the cassette.

The portable fixing device 5200 serves to cause the cassette mounted on the bucky tray 5000 to coincide with the central vertical line 551 of the bucky and to firmly and safety fix the cassette 5000. In order to fix the electronic cassette provided with the handle, the portable fixing device 5200 is located at the upper end of the bucky tray. The portable fixing device 5200 includes one driving motor 5205, two portable fixing bodies 5210 and 5220, two fixing rails 5211 and 5221, and two portable fixing shafts 5212 and 5222. Each of the portable fixing bodies 5210 and 5220 includes a portable fixing support 5213, a portable fixing handle 5214, and a portable fixing protrusion 5215.

When the fixing sensors 5215 of the safety fixing devices 5110 and 5210 are operated, an operating command is transmitted to the driving motor 5205 of the portable fixing device 5220, the driving motor is driven in the clockwise direction so as to drive the two portable fixing shafts 5212 and 5222 in the central direction, the portable fixing shafts move the portable fixing bodies 5219 and 5220 to the center of the bucky tray, and the fixing protrusions 5215 of the portable fixing bodies fix the cassette. Particularly, in case of the electronic cassette, the fixing protrusions 5215 are engaged with the fixing grooves 3051~3056 and 3251~3252 of the electronic cassette so as to firmly and safely fix the electronic cassette. Mount sensors 5216 of the fixing bodies 5210 and 5220 are located within the edge where the fixing bodies and the cassette are engaged with each other. Sensing of the cassette by the mount sensors of the portable fixing bodies 5210 and 5220 means that the cassette is precisely mounted at the center of the bucky. Then, the mount state of the cassette is transmitted to the X-ray generation and bucky control unit 121 and the position displays 5631~5638 and 5731~5738 are turned on, thereby completing the mount preparation of the cassette.

The portable fixing bodies 5210 and 5220 move by the same distance from the center of the bucky tray, and thus the central vertical line $3041v$, $3042v$, $3241v$, $411v$, or $421v$ of the mounted cassette coincides with the central vertical line 551 of the bucky 500 at all times. If the central vertical line $3041v$, $3042v$, $3241v$, $411v$, or $421v$ of the mounted cassette does not coincide with the central vertical line 551, the two mount sensors do not sense the cassette and the position displays 5631~5638 and 5731~5738 are not turned on, and thereby the mount preparation of the cassette is not completed.

Under the condition that the cassette is fixed to the portable fixing bodies 5210 and 5220 and the fixing sensors 5216 of the fixing bodies sense the cassette, when a designated pressure is again applied to the safety fixing devices 5110 and 5120, the fixing sensors 5115 recognize the mount state of the detector and transmit an operating signal of the portable fixing device 5200, and the operating signal operates the motor 5205 of the portable fixing device in the counterclockwise direction to move the portable fixing bodies 5210 and 5220 outwards, thereby releasing fixation of the cassette. At this time, the safety fixing devices fix the cassette, and thus prevent the cassette from being separated from the bucky tray 5000 and then being damaged due to user's carelessness.

Figure 16:
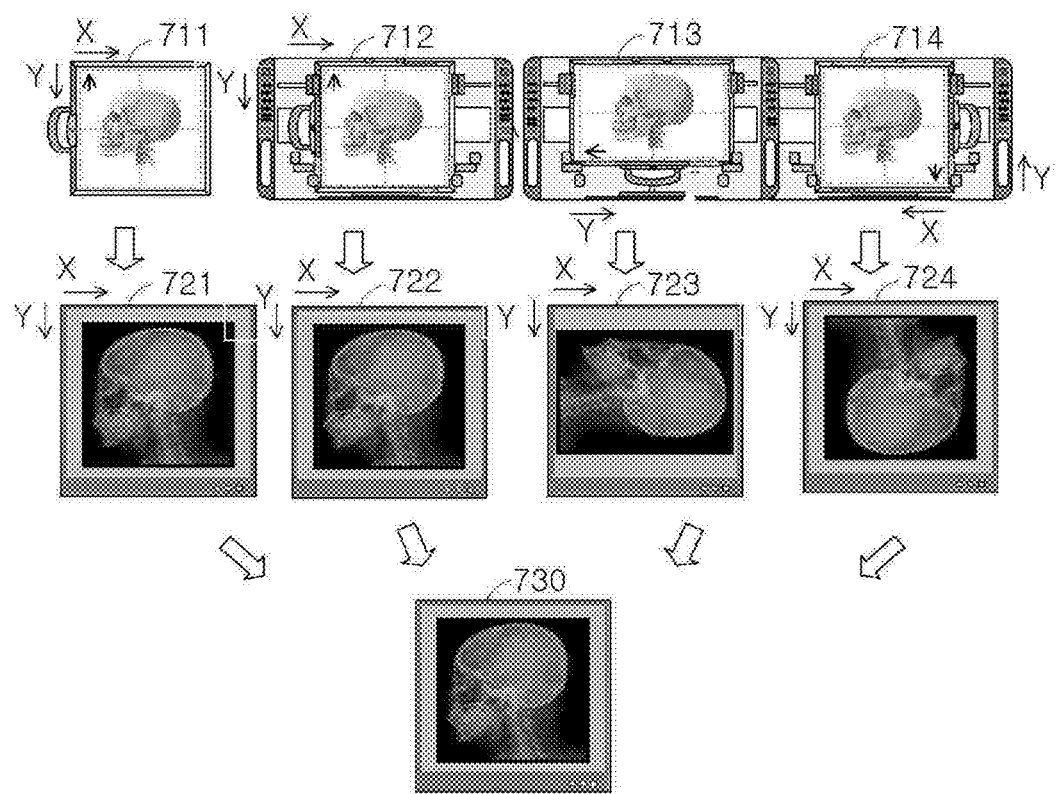
FIG. 16 is an exemplary view illustrating an automatic image correcting process according to a bucky tray mount state.

The ID chip reader 5061 of the bucky tray 5000 is located at the upper end of the center of the bucky tray, and, when the mount sensors 5216 transmit the normal mount state of the cassette to the X-ray generation and bucky control unit 121, the ID chip reader reads a serial number of the ID chip 3061, 3062, 3063 or 3261 of the electronic cassette and transmits the serial number of the electronic cassette to the X-ray generation and bucky control unit 121 (FIG. 16(*a*)). The X-ray generation and bucky control unit 121 transmits the serial number to the application program provision unit 111 and the communication and image acquisition unit 131. The application program provision unit transmits the serial number to the pre-processing unit, and the pre-processing unit searches a pre-processing file suitable for the serial number and performs a preparation to apply the pre-processing file when an image is acquired. The application program provision unit 111 requests the communication and image acquisition unit 131 to give channel data of the electronic cassette mounted within the bucky, receives the channel data from the communication and image acquisition unit 131, and transmits the channel data to the X-ray generation and bucky control unit, and the X-ray generation and bucky control unit displays the channel data on the channel display units of the bucky. If the ID chip is not read, the X-ray generation and bucky control unit 121 judges that the image plate cassette or the film cassette is mounted (FIG. 15(*b*)).

The power supply unit 5070 of the bucky tray 5000 supplies power to the bucky tray, if the mounted electronic cassette 3111 and 3211 is connected to the workstation wirelessly.

The power supply unit 5070 is located at the upper end of the center of the bucky tray, and includes a power supply pin 5071, a ground pin 5072, and a sensor pin 5073. When the wirelessly connected electronic cassette is mounted on the bucky tray, the sensor pin 5073 contacts the sensor terminal 3072 of the electronic cassette 3111, as shown in FIG. 15(a), and, when the contact state is normal, power is supplied to the electronic cassette through the power supply pin. If the sensor pin does not contact the sensor terminal of the electronic cassette, it is judged that the electronic cassette is not normally mounted on the bucky tray, power supply is cut off, and the application program provision unit is requested to give a message requiring a mount state checkup through the X-ray generation and bucky control unit 121. Instead of the above contact power supply method, a non-contact power supply method may be used.

FIG. 16 illustrates automatic direction correction of the mounted large area electronic cassette. The bucky 5000 in accordance with the present invention allows the large area electronic cassette 3111 to be mounted thereon in both directions. The electronic cassette may be mounted in three forms 712, 713, and 714. When the large area electronic cassette 3111 is mounted in the forward direction 711 or 712, a normal image 721 or 722 is acquired. However, the large area electronic cassette 3111 is mounted in the reverse direction 714 or horizontally mounted 713, an image 723 rotated by an angle of 90° or an image 724 rotated by an angle 180° is acquired. In this case, if a user does not recognize the right and left directions of the acquired image under the condition that the large area electronic cassette is mounted within the bucky and thus the mount state of the large area electronic cassette is not easily recognized, directionality of the image is lost and thus confusion between the right and left sides of the image may occur. At this time, when the image is displayed in the wrong direction and then the image is read, an error in image diagnosis may occur. In order to prevent such an error, the direction of the image is automatically corrected according to the mount state of the electronic cassette.

Automatic image direction correction requires recognition of the mount state of the electronic cassette. The electronic ID chips 3061, 3062, and 3063 are located on the rear surface of the electronic cassette, and serve to the mount state of the electronic cassette on the bucky to be recognized. When the electronic cassette is mounted in the reverse direction 714, the ID chip reader 5061 reads the electronic ID chip 3061 and the acquired image 724 is rotated by an angle of 180° to automatically produce a precise image 730. Further, when the electronic cassette is mounted horizontally 713, the ID chip reader 5061 reads the electronic IC ship 3062 and the acquired image 723 is rotated by an angle of 90° to automatically produce the precise image 730.

The application program control unit 110 recognizes the mount state of the electronic cassette and then the acquired image is rotated by an angle of 90° or 180°. Thereby, a user may detect the image, the direction of which coincides with the actual direction of the radiographed body of a patient, at all times, thereby rapidly conducting an inspection while avoiding direction confusion.

Figure 17:
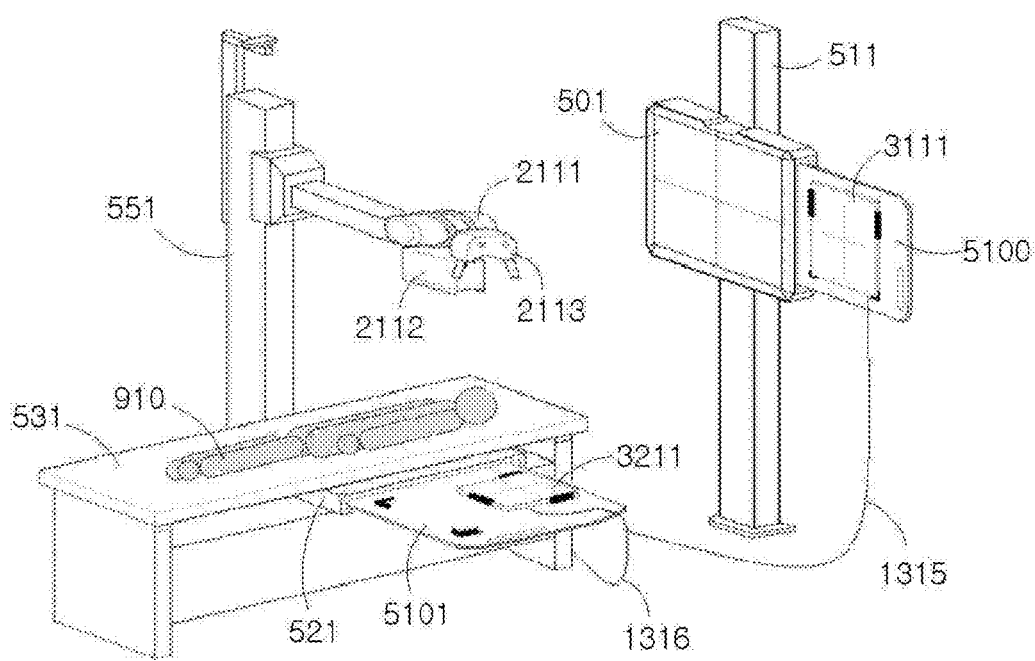
FIG. 17 is a perspective view of the digital radiography system using electronic cassettes.
Figure 18:
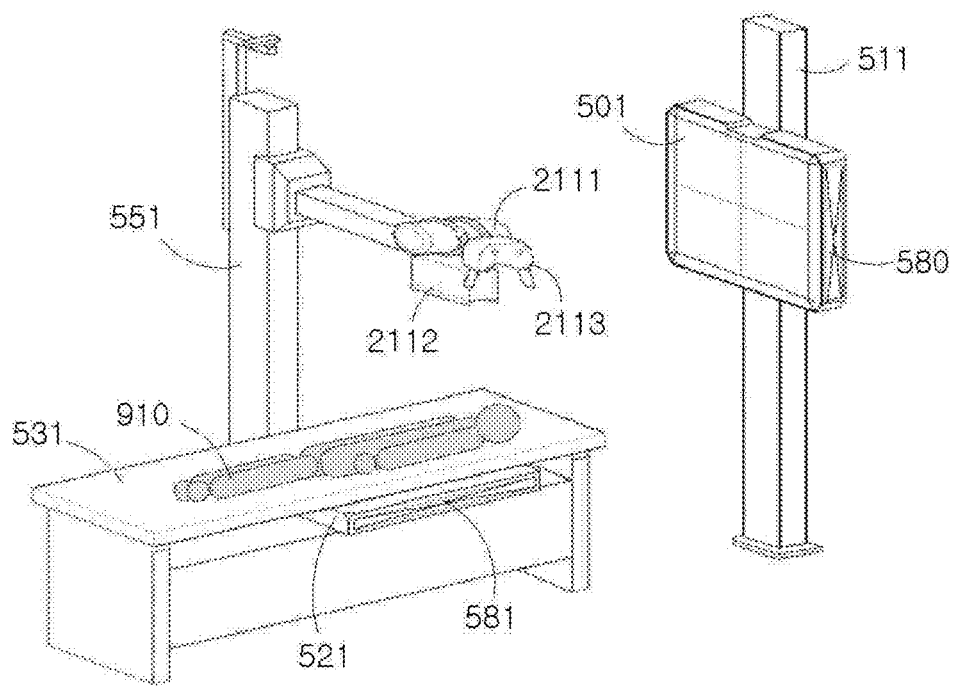
FIG. 18 is a perspective view of a digital radiography system using fixed flat panel detectors.
Figure 19:
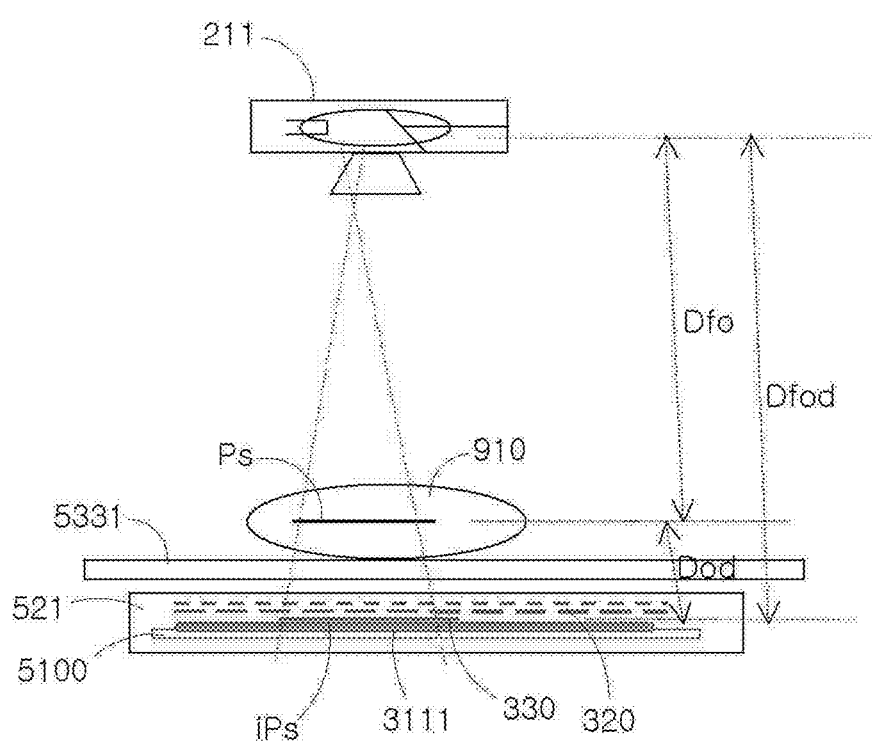
FIG. 19 is a longitudinal-sectional view illustrating photography using the bucky.

FIG. 17 is a perspective view of the digital radiography system in accordance with the present invention in which the electronic cassettes 3111 and 3211 are mounted on bucky trays. The small area electronic cassette 3211 is mounted on the bucky tray 5101 of the table bucky 521, and the large area electronic cassette 3111 is mounted on the bucky tray 5100 of the stand bucky. The electronic cassettes are connected to the workstation 101 by wire 1315 and 1316 or wirelessly 1317 and 1318, such that the workstation 101 controls the electronic cassettes. Since the electronic cassettes are freely mounted on and detached from the bucky trays and are divided into the large area electronic cassette and the small area electronic cassette, the digital radiography using the electronic cassettes may be easily used in radiography on a fixed table and radiography on a bed of an emergent patient or a serious patient as well as radiography using buckies.

MODE FOR INVENTION

Various embodiments have been described in the best mode for carrying out the invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A digital radiography system comprising:
a plurality of portable electronic cassettes;
bucky trays on each of which a portable electronic cassette of the plurality of portable electronic cassettes is detachably mounted; and
a workstation connected with the bucky trays through communication to identify the plurality of portable electronic cassettes and to control pre-processing files of the identified plurality of portable electronic cassettes,
wherein the workstation includes:
a pre-processing unit to apply the pre-processing files corresponding to the plurality of portable electronic cassettes; and
a communication and image acquisition unit provided with channels to communicate with the plurality of portable electronic cassettes to acquire radiography images,
wherein the pre-processing unit includes the pre-processing files corresponding to the plurality of portable electronic cassettes and a network to communicate with other pre-processing units, and
wherein the pre-processing unit has a function of searching pre-processing files applied to a portable electronic cassette of the plurality of portable electronic cassettes connected to the digital radiography system, and first applying the latest pre-processing files among the searched pre-processing files.

2. The digital radiography system according to claim 1, wherein the digital radiography system further comprises a network and a portable storage device, and the workstation transmits the pre-processing files of the plurality of portable electronic cassettes mounted on the bucky trays to other workstations provided in other digital radiography systems through the network and the portable storage device.

3. The digital radiography system according to claim 2, wherein the workstation has a function of preventing increase in an amount of radiation exposed to a patient caused by a radiography mistake due a mount error, a radiography position error, and a setting error of the portable electronic cassette.

4. The digital radiography system according to claim 3, wherein the workstation checks a mount form of the portable electronic cassette through sensors, and performs image position correction using the sensors.

5. The digital radiography system according to claim 1, wherein each bucky tray of the bucky trays has a function of identifying a portable electronic cassette of the plurality of portable electronic cassettes mounted thereon in order to prevent confusion generated when the plurality of portable electronic cassettes is used in the digital radiography system.

6. The digital radiography system according to claim 5, wherein each bucky tray of the bucky trays includes safety fixing devices to prevent damage to the portable electronic cassette due to operator's carelessness.

7. The digital radiography system according to claim 6, wherein each safety fixing device includes a sensor to recognize the normal mount state of the portable electronic cassette.

8. The digital radiography system according to claim 6, wherein each bucky tray of the bucky trays further includes two portable fixing devices to cause the portable electronic cassette to coincide with a central vertical line.

9. The digital radiography system according to claim 8, wherein each portable fixing device includes a sensor to recognize the mount state of the portable electronic cassette,
wherein each portable fixing device further includes a protruding portion to firmly and stably fix the portable electronic cassette.

10. The digital radiography system according to claim 5, wherein each bucky tray of the bucky trays further includes channel display units to display a channel of the mounted portable electronic cassette.

11. The digital radiography system according to claim 10, wherein the digital radiography system further comprises a mounted image plate cassette and a film cassette, and each bucky tray of the bucky trays further includes position display units to identify a kind of the mounted portable electronic cassette or the mounted image plate cassette or the film cassette and to display a central horizontal line according to the kind and size of the cassette.

12. The digital radiography system according to claim 11, wherein each bucky tray of the bucky trays further includes a code reader to read an identification code provided on the portable electronic cassette,
wherein each bucky tray of the bucky trays further includes a power supply unit to supply power to the portable electronic cassette.

13. The digital radiography system according to claim 1, wherein each portable electronic cassette of the plurality of portable electronic cassettes includes a channel display unit to display a channel connected to the workstation,
wherein each portable electronic cassette of the plurality of portable electronic cassettes further includes an electronic cassette selection switch to identify the portable electronic cassette on which radiography is to be carried out.

14. The digital radiography system according to claim 13, wherein each portable electronic cassette of the plurality of portable electronic cassettes further includes at least one identification code to identify the portable electronic cassette.

15. The digital radiography system according to claim 14, wherein each portable electronic cassette of the plurality of portable electronic cassettes further includes a power terminal to receive power supplied from the bucky tray.

16. The digital radiography system according to claim 15, wherein each portable electronic cassette of the plurality of portable electronic cassettes further includes at least two depressed portions to be firmly fixed to the portable fixing devices of the bucky tray.

\* \* \* \* \*